(12) United States Patent
Ulitin et al.

(10) Patent No.: US 10,442,857 B2
(45) Date of Patent: Oct. 15, 2019

(54) ANTI-IL-17 ANTIBODIES

(71) Applicant: CLOSED JOINT STOCK COMPANY "BIOCAD", Strelna, Petrodvortsoviy district, Saint Petersburg (RU)

(72) Inventors: Andrey Borisovich Ulitin, Puschino Moskovskaya obl. (RU); Stanislav Rudolfovich Evdokimov, Puschino Moskovskaya obl. (RU); Valeriy Vladimirovich Soloviev, Puschino Moskovskaya obl. (RU); Yulia Sergeevna Chernyh, Solikamsk Permsky kray (RU); Olga Vladimirovna Goncharova, Lyubuchany Chekhovskiy r-n Moskovskaya.obl (RU); Dmitriy Valerievich Korzhavin, St.Petersburg (RU); Tatyana Veniaminovna Chernovskaya, Lyubuchany Chekhovskiy r-n Moskovskaya.obl (RU); Roman Alexeevich Ivanov, Moscow (RU); Dmitriy Valentinovich Morozov, Moscow (RU)

(73) Assignee: CLOSED JOINT STOCK COMPANY "BIOCAD", Saint Petersburg (RU)

( * ) Notice: Subject to any disclaimer, the term of this patent is extended or adjusted under 35 U.S.C. 154(b) by 0 days.

(21) Appl. No.: 15/254,190

(22) Filed: Sep. 1, 2016

(65) Prior Publication Data

US 2017/0081401 A1     Mar. 23, 2017

Related U.S. Application Data

(63) Continuation of application No. PCT/RU2014/000808, filed on Oct. 27, 2014.

(30) Foreign Application Priority Data

Mar. 14, 2014  (RU) ................................ 2014109854

(51) Int. Cl.
| | |
|---|---|
| *A61K 39/395* | (2006.01) |
| *C07K 16/24* | (2006.01) |
| *A61K 45/06* | (2006.01) |
| *A61K 39/00* | (2006.01) |

(52) U.S. Cl.
CPC ........ *C07K 16/244* (2013.01); *A61K 39/3955* (2013.01); *A61K 45/06* (2013.01); *A61K 2039/505* (2013.01); *C07K 2317/22* (2013.01); *C07K 2317/24* (2013.01); *C07K 2317/33* (2013.01); *C07K 2317/51* (2013.01); *C07K 2317/515* (2013.01); *C07K 2317/52* (2013.01); *C07K 2317/55* (2013.01); *C07K 2317/565* (2013.01); *C07K 2317/76* (2013.01); *C07K 2317/90* (2013.01); *C07K 2317/92* (2013.01); *C07K 2317/94* (2013.01); *Y02A 50/386* (2018.01); *Y02A 50/41* (2018.01); *Y02A 50/412* (2018.01)

(58) Field of Classification Search
None
See application file for complete search history.

(56) References Cited

U.S. PATENT DOCUMENTS

2013/0131319 A1   5/2013  Igawa et al.

FOREIGN PATENT DOCUMENTS

| WO | 2007149032 A1 | 12/2007 |
| WO | 2008021156 A2 | 2/2008 |

OTHER PUBLICATIONS

Chen et al. "In vitro scanning saturation mutagenesis of all the specificity determining residues in an antibody binding site." Protein Engineering, 1999, vol. 12, No. 4, pp. 349-356.
International Search Report with regard to PCT/RU2014/000808 dated Apr. 9, 2015.

*Primary Examiner* — Dong Jiang
(74) *Attorney, Agent, or Firm* — Anglehart et al.

(57) ABSTRACT

The present invention relates to the field of medicine, and specifically to the field of monoclonal antibodies against human IL-17. More specifically, the invention relates to monoclonal antibodies/antagonists of IL-17A, which bind with high affinity to an IL-17 epitope, wherein the antibodies contain amino acid substitutions in hypervariable regions of heavy and light chains. The antibodies according to this invention can be chimeric, humanized or human antibodies or antigen-binding fragments thereof, and can be used as a medicinal agent for treating autoimmune and inflammatory disorders and disorders of cell proliferation and development. The invention also relates to methods for producing said antibodies.

16 Claims, 13 Drawing Sheets
Specification includes a Sequence Listing.

A human Fab phage library

| Concentration (nm) | Signal | KD (M) | kon(1/Mc) | Deviation kon | kdis(1/c) | Deviation kdis | Absolute square deviation R^2 |
|---|---|---|---|---|---|---|---|
| 68.6 | 1.2507 | <1.0E-12 | 2.20E+05 | 6.80E+02 | <1.0E-07 |  | 0.973327 |
| 34.3 | 1.0595 | <1.0E-12 | 2.64E+05 | 1.77E+03 | <1.0E-07 |  | 0.937248 |

| Concentration (nm) | Signal | KD (M) | kon(1/Mc) | Deviation kon | kdis(1/c) | Deviation kdis | Absolute Square deviation R^2 |
|---|---|---|---|---|---|---|---|
| 68.7 | 0.3246 | 5.97E-09 | 1.61E+05 | 2.73E+03 | 9.60E-04 | 2.35E-05 | 0.956946 |
| 34.4 | 0.2032 | 4.15E-09 | 2.71E+05 | 4.78E+03 | 1.13E-03 | 2.31E-05 | 0.964905 |
| 17.2 | 0.127 | 2.22E-09 | 4.06E+05 | 6.23E+03 | 9.01E-04 | 1.71E-05 | 0.983707 |

| № | Time | Area | Height | Width | % Area | Symmetry | Sample MMt |
|---|---|---|---|---|---|---|---|
| 1 | 7.371 | 147.8 | 4.4 | 0.4004 | 1.062 | 0.809 | 274666,2 |
| 2 | 8.656 | 13246 | 642.7 | 0.3165 | 95.157 | 0.876 | 149758,8 |
| 3 | 9.216 | 402.6 | 24.6 | 0.2272 | 2.892 | 0.283 | 52237,09 |
| 4 | 10.663 | 123.8 | 7 | 0.2528 | 0.889 | 0.867 | 33009,53 |

US 10,442,857 B2

ANTI-IL-17 ANTIBODIES

CROSS-REFERENCE

The present application claims convention priority to Russian Utility Patent Application No. 2014109854, filed on Mar. 14, 2014, entitled "АНТИ-IL-17 АНТИТЕЛА, СПОСОБ ИХ ПОЛУЧЕНИЯ И СПОСОБ ПРИМЕНЕНИЯ". This application is incorporated by reference herein in its entirety. The present application is a continuation of International Patent Application no. PCT/RU2014/000808, filed on Oct. 27, 2014, entitled "ANTI-IL-17 ANTIBODIES, METHOD FOR PRODUCING SAME AND METHOD FOR USING SAME". This application is incorporated by reference herein in its entirety.

FIELD OF INVENTION

The present invention relates to the field of medicine, in particular, to the field of monoclonal antibodies against human IL-17. More particular, this invention relates to monoclonal antibodies—IL-17A agonists which bind with a high affinity to IL-17 epitopes, wherein these antibodies comprise amino acid substitutions in hypervariable regions of heavy and light chains. Antibodies of the invention can be chimeric, humanized or human antibodies or antigen-binding fragments thereof, and can be used as a medicinal agent for the treatment of autoimmune and inflammatory disorders or cell proliferative and developmental disorders. This invention also relates to a method for preparing the said antibodies.

BACKGROUND OF THE INVENTION

The key function of immune system is to protect the body from infections (for example, viral or bacterial) and malignant neoplasms. The system involves several types of lymphoid and myeloid cells such as monocytes, macrophages, dendrite cells, eosinophils, T-cells, B-cells and neutrophils. These lymphoid and myeloid cells can induce the signal proteins known as cytokines. Inflammation is a part of immune response and causes the accumulation of immune cells, either systemic or centered in certain parts of the body. When responding to the infection or any foreign substance, immune cells release cytokines which, in their turn, modulate immune cell proliferation, development, differentiation and migration. The immune response can induce various pathological processes, for example, if it triggers the excessive inflammation as it happens in case of autoimmune diseases (ref. Abbas et al. (eds.) (2000) Cellular and Molecular Immunology, W.B. Saunders Co., Philadelphia, Pa.; Oppenheim and Feldmann (eds.) (2001) Cytokine Reference, Academic Press, San Diego, Calif.; von Andrian and Mackay (2000) New Engl. J. Med. 343:1020-1034; Davidson and Diamond (2001) New Engl. J. Med. 345:340-350).

Today the IL-17 family includes IL-17A, IL-17B, IL-17C, IL-17D, IL-17E and IL-17F. All members of IL-17 family have four highly conserved cysteine residues which are involved in the formation of inter-chain disulfide bonds, and two or more cysteine residues which also may be involved. Members of IL-17 family have nothing similar to the sequences of other known cytokines.

Interleukin-17A (IL-17A, also known as cytotoxic T-lymphocyte-associated antigen-8 (CTLA-8), IL-17) is a homodimeric cytokine of 20-30 kDa produced by memory T-cells with the following antigen recognition. The growth of these T-cells is promoted by interleukin-23 (IL-23) (McKenzie et al. (2006) Trends Immunol. 27(1):17-23; Langrish et al. (2005) J. Exp. Med. 201(2):233-40). IL-17A acts via two receptors (IL-17RA and IL-17RC) to initiate the production of multiple molecules involved in the processes with neutrophils, inflammatory processes and organ damage. This cytokine is synergetic with tumor necrosis factor (TNF) or interleukin 1-beta (IL-1β) to achieve a more pronounced anti-inflammatory effect. In the therapy of many inflammatory, immune and proliferative conditions including rheumatoid arthritis (RA), osteoarthritis, osteoporosis in patients with RA, inflammatory fibrosis (including scleroderma, pulmonary fibrosis and cirrhosis), gingivitis, periodontitis or periodontal diseases, inflammatory bowel diseases (for example, Crohn's disease, ulcerative colitis and inflammatory bowel disease), asthma (including the allergic asthma), allergies, chronic obstructive pulmonary disease (COPD), multiple sclerosis, psoriasis, cancer and other disorders it was proposed to reduce IL-17A activity by means of antibodies or antigen-binding antibody fragments which block said receptors (for example, refer to US 2003/0166862, WO 2005/108616, WO 2005/051422 and WO 2006/013107).

At the present time, several types of anti-IL-17 antibodies were developed including AIN457 (secukinumab by Abbott Laboratories), LY2439821 (Ixekizumab by Eli Lilly), SCH900117 (Merck), RG4943 (Roche), etc.

For example, the US Patent application US 2010/0245666 describes anti-IL-17 antibody (secukinumab, AIN457) that contains an amino acid substitution or deletion in one of CDR regions of the heavy or light chains. This antibody is highly affine to IL-17 with dissociation constant $K_D$ of about 122 μM. This application also discloses the use of said antibodies to inhibit IL-17 binding with an appropriate receptor, especially for the treatment of uveitis. Currently, the said antibody undergoes the clinical trials for the treatment of RA, ankylosing spondyloarthropathy, Crohn's disease, psoriasis, multiple sclerosis and ozone-induced neutrophilia. It was shown that this antibody is safe and exhibits 46% efficacy in patients with RA (Durez et al., Communication EULAR 2009-RA).

The prior knowledge has also disclosed the humanized antibodies against IL-17 as described in the international publication of WO 2007/070750 application (LY2439821, ixekizumab, Eli Lilly). Said antibodies contain variable heavy and light chain domains with amino acid substitutions. Upon that, the said antibody is highly affine to human IL-17 (KD is lower than about 7.0-4.0 pM) and has koff index for human IL-17<$2 \times 10^{-5}$ sec$^{-1}$. Antibodies were subject clinical studies of the safety, tolerability and efficacy upon intravenous administration in subjects with RA. (Genoevse et al., Communication EULAR 2009-RA; Genoevse et al., *Arthritis & Rheumatism*, 62: 929-39, (2010).

The prior state of art has information on other anti-IL-17 antibodies: murine anti-human neutralizing antibodies eBio64CAP17 (eBioscience) and derivatives thereof. Other examples of anti-IL-17 antibodies were disclosed in patent applications US2009/0175881A1 and US2008/0269467A1, and in international publications WO2008/001063A1 and WO2007/117749A1.

Thus, taking into account its localized expansion in the area of inflammation, IL-17 is a new target in the therapy of inflammatory and autoimmune disorders, with the safety profile potentially higher than drugs targeting the systemic circulation proinflammatory cytokines such as TNF (tumor necrosis factor). In view of the above said, it can be concluded that there is a need for antibodies having antagonistic activity or neutralizing the activity of IL-17A for treating the diseases and conditions, wherein the biological activity of IL-17A causes or promotes the adverse pathological result, or diseases and conditions, wherein the reduction of IL-17 biological activity promotes the desirable therapeutic result, including inflammatory disorders, cell proliferative and developmental disorders, autoimmune pathologies such as rheumatoid arthritis (RA) and inflammatory bowel disease (IBD).

The largest limitations of using antibodies as medicinal agents are due to their immunogenicity and affinity. Since the majority of monoclonal antibodies are obtained on the basis of murine ones, the regular use of such antibodies in humans causes the development of immune response to antibody therapy (for example, allergic reactions). These types of immune response finally result in the lack of efficacy at least, and in potential anaphylactic reactions at worst.

Thus, the present invention suggests anti-IL-17 antibodies with amino acid substitutions, wherein the claimed antibodies possess high affinity, improved solubility and increased $IC_{50}$.

BRIEF DESCRIPTION OF THE DRAWINGS

FIG. 3A shows a 12% SDS-PAGE under reducing conditions, wherein:
Lane 1 is AIN457 2.5 µg;
Lane 2 is AIN457 5 µg;
Lane 3 is AIN457 0 µg;
Lane 4 is Enzyme-unstained PW Marker;
Lane 5 is IgG aIL17 A1CL v4C2P 5 µL;
Lane 6 is IgG aIL17 A1CL v3E2P 5 µL;
Lane 7 is IgG aIL17 A1CL v1A2C 5 µL;
Lane 8 is IgG aIL17 A1CL v7C2P 5 µL;
Lane 9 is IgG aIL17 A1CL v1D2C 5 µL;
Lane 10 is IgG aIL17 A1CL v2D2C 5 µL;
Lane 11 is IgG aIL17 A1CL v4D2P 5 µL; and
Lane 12 is IgG aIL17 A1CL control.
FIG. 3B shows a 12% SDS-PAGE under non-reducing conditions, wherein:
Lane 1 is AIN457 2.5 µg;
Lane 2 is AIN457 5 µg;
Lane 3 is AIN457 0 µg;
Lane 4 is Enzyme-unstained PW Marker;
Lane 5 is IgG aIL17 A1CL v4C2P 5 µL;
Lane 6 is IgG aIL17 A1CL v3E2P 5 µL;
Lane 7 is IgG aIL17 A1CL v1A2C 5 µL;
Lane 8 is IgG aIL17 A1CL v7C2P 5 µL;
Lane 9 is IgG aIL17 A1CL v1D2C 5 µL;
Lane 10 is IgG aIL17 A1CL v2D2C 5 µL;
Lane 11 is IgG aIL17 A1CL v4D2P 5 µL; and
Lane 12 is IgG aIL17 A1CL control.
FIG. 15A shows an Interaction curve for BCD085 with human IL-17.
FIG. 15B shows a table indicating data points derived from the interaction curve of FIG. 15A.
FIG. 16A shows an Interaction curve for BCD085 with monkey IL-17 (Macaca mulatta).
FIG. 16B shows a table indicating data points derived from the interaction curve of FIG. 16A.
FIG. 17A shows a Chromatogram obtained with BCD085 antibody after the thermal stress.
FIG. 17B shows a table indicating data points derived from the interaction curve of FIG. 17A.

SPECIFICATION OF INVENTION

Definitions

"Interleukin 17", also referred to as "IL-17" or "IL-17A", is a 20-30 kD homodimeric glycoprotein. The gene of human IL-17 encodes the protein consisting of 155 amino acids and having a 19 amino acid signal sequence and 136 amino acid mature segment. A full-size antibody as it occurs in nature is represented by immunoglobulin (antibody) molecule consisting of four peptide chains: two heavy (H) chains (about 50-70 kD full length) and two light (L) chains (about 25 kD full length) linked with disulfide bonds. Amino terminal domain of each chain includes a variable region of about 100-110 or more amino acids which is mostly responsible for antigen recognition. Carboxyl-terminal domain of each chain determines the constant region mostly responsible for the effector function.

Figure 19:
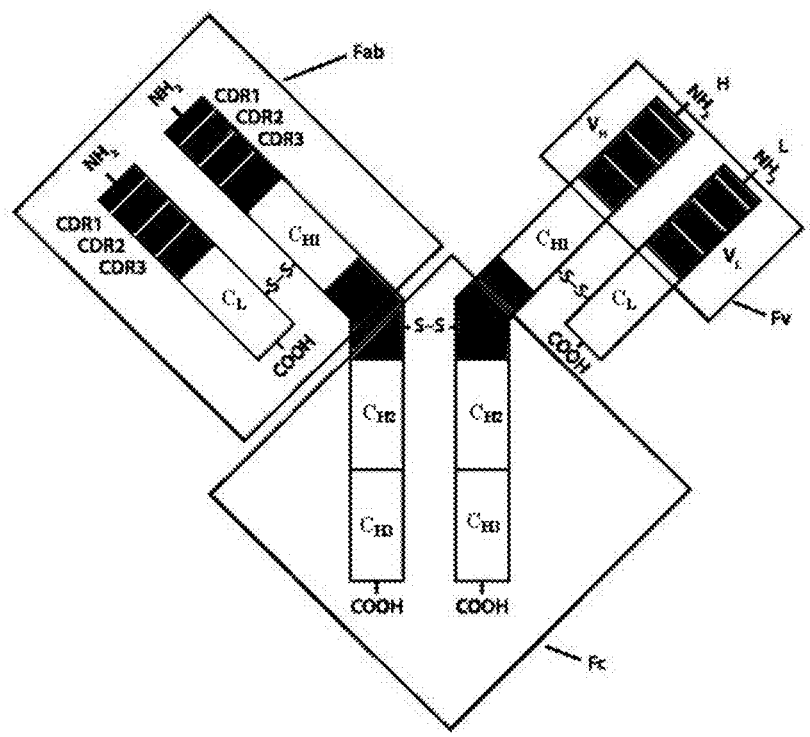
FIG. 19 shows a schematic representation of the structure of an IgG-type antibody.

Antibody comprises of the light and heavy chains. Variable domains of the heavy and light chains form an antigen-binding center (site). The antibody structure is presented in FIG. 19.

Light chains are classified as kappa and lambda and have specific constant regions. Each light chain is characterized in comprising a variable N-terminal light chain region (herein referred to as LCVR or VL) and a constant light chain region which consists of a single domain (CL). Heavy chains are classified as γ, δ, α, μ and ε and define classes of immunoglobulins: IgG, IgM, IgA, IgD and IgE, respectively; some of them can be additionally divided into sub-classes (isotypes) such as IgG1, IgG2, IgG3, IgG4, IgA1 and IgA2. Each heavy chain type is characterized by a specific constant region Fc. Each heavy chain comprises a variable N-terminal region (herein referred to as HCVR or VH) and constant region CH. Constant heavy chain region consists of three domains (CH1, CH2 and CH3) for IgG, IgD and IgA, and of 4 domains (CH1, CH2, CH3 and CH4) for IgM and IgE. HCVR and LCVR can be also divided into so-called hypervariable regions Rf (complementarity determining regions, CDR) interspersing with more conservative framework regions (FR). Each HCVR and LCVR comprises three CDRs and FRs located in the following order from N-terminus to C-terminus: FR1, CDR1, FR2, CDR2, FR3, CDR3 and FR4. In the present application 3 heavy chain CDRs are referred to as CDRH1, CDRH2 and CDRH3, while 3 light chain CDR are referred to as CDRL1, CDRL2 and CDRL3. CDRs contain the majority of amino acid residues specifically interacting with the antigen. According to the present invention, CDR-residues in HCVR and LCVR are numbered and positioned in compliance with the Kabat Numbering Scheme, unless otherwise stated. The present application includes the common letter codes for amino acids, unless otherwise stated.

The terms "anti-IL-17A antibody", "antibody against IL-17", "antibody specifically binding to interleukin IL-17" and "antibody against IL-17A" are interchangeable herein and relate to an antibody specifically binding to IL-17A.

As used herein, the term "antibody" in relation with anti-IL-17A monoclonal antibody of the present invention (or in a simplified form: "monoclonal antibody according to the invention"), relates to a monoclonal antibody. "Monoclonal antibody", as used herein, relates to an antibody obtained from rodents, primates or Camelidae family, preferably to murine, monkey, camel or llama antibody, chimeric antibody, humanized antibody or fully human antibody, unless otherwise stated in the present application. Monoclonal antibodies according to the invention can be produced using hybridoma technology known from the prior art, recombinant technology, phage display technology, synthetic technology or the combinations of these or other technologies well known from the prior art. The term "monoclonal antibody", as used herein, is not limited by antibodies obtained by means of hybridoma technology. "Monoclonal antibody" refers to an antibody obtained from a single copy or clone including, for example, any eukaryotic, prokaryotic or phage clone, rather than to production method thereof. "Monoclonal antibody" can be an intact antibody (with full or full-length Fc-region), actually intact antibody, an antibody part or fragment comprising an antigen-binding region, for example, Fab-fragment, Fab'-fragment or F(ab')2-fragment. "Fab"-fragment comprises a variable light chain domain and a constant light chain domain as well as a variable heavy chain domain and first constant heavy chain domain (CH1). "F(ab')2" antibody fragment contains a pair of Fab-fragments which are mostly covalently bound by hinged amino acids at C-terminal regions. Fv is a variable antibody fragment; scFv (single chain Fv) is a variable fragment of an antibody in which light and heavy chain fragments are linked via a short linker peptide; (scFv)2—fragment consisting of two scFv molecules bound with disulfide bond; dsFv—variable fragment stabilized with additional intramolecular disulfide bond. Other chemical bonds between antibody fragments are also well known from the state of art.

Terms "antibody" and "immunoglobulin" are interchangeable as used herein.

Variable regions of each of the light/heavy chain pair form an antigen-binding site of an antibody. According to the present application, "antigen-binding region" or "antigen-binding site", or "antigen-binding domain", or "antigen-binding center" are interchangeable, as used herein, with refer to an antibody region comprising amino acid residues interacting with an antigen and giving the antibody its specificity and affinity to an antigen. This antibody fragment includes the frame amino acid residues necessary for maintaining the proper conformation of antigen-binding residues.

Preferably, CDR of an antigen-binding region or the entire antigen-binding site in accordance with the invention originates from a donor human library or is basically of a human origin, and has specific amino acid residues changed, for example, substituted with various amino acid residues in order to improve the particular properties of an antibody (for example, its $K_D$, $k_{off}$ and $IC_{50}$). Preferably, the antibody framework regions in accordance with the invention are of a human origin or substantially of a human origin (at least by 80, 85, 90, 95, 96, 97, 98 or 99% of human origin). Preferable framework regions of an antibody in accordance with the invention have amino acid sequences corresponding to framework regions of the human antibody:

Variable Domain of the Heavy Chain

```
FR1
QVQLVQSGGGLVQPGGSLRLSCAADG

FR2
WVRQAPGKGLEWVS

FR3
RFTISRDDAKNTLYLQMSSLKTEDTAVYYC

FR4
WGQGTLVTVSS
```

Variable Domain of the Light Chain

```
FR1
QSVLTQPPSVSVAPGKTVTISC

FR2
WYQHLPGTAPKLLIY

FR3
GVPDRFSGSQSGNTASLTISGLQAEDEADYYC

FR4
FGGGTKLTVLGQ.
```

In another embodiments, an antigen-binding site of anti-IL-17 antibody of the invention can originate from other non-human species including but not limited to rabbit, rat or hamster. Alternatively, antigen-binding site can originate from human species.

Besides, a "monoclonal antibody" according to the present application can be represented by a single-chain Fv-fragment which can be obtained by binding of LCVR- and HCVR-encoding DNA with a linker sequence (refer to Pluckthun, The Pharmacology of Monoclonal Antibodies, vol. 113, Rosenburg and Moore eds., Springer-Verlag, New York, p. 269-315, 1994). It is understood that independently on whether fragments or parts are specified, the term "antibody" as used in the present application includes such fragments or parts as well as single-chain forms. Until the protein keeps its ability of specific or preferred binding to the target (epitope or antigen, for example), it is covered by the term "antibody". Antibodies can be either glycosylated or not and are within the frames of the invention.

The population of "monoclonal antibodies", as used herein, refers to a homogenous or essentially homogeneous antibody population (i.e. at least about 85, 90, 91, 92, 93, 94, 95, or 96%, but more preferably no less than about 97 or 98%, or further preferably at least 99% of antibodies in the population will compete for the same antigen/epitope in ELISA, or further preferably antibodies are identical regarding their amino acid sequences). Antibodies can be either glycosylated or not, yet still be within the scope of the invention. Monoclonal antibodies are homogenous if they have identical amino acid sequence, yet they can differ in post-translation modification (for example, glycosylation patterns).

Antibody "variant", as used herein, refers to a molecule amino acid sequence of which differs from the parental sequence by adding, deletion and/or substitution of one or more amino acid residues in the sequence of parental antibody. In the preferred embodiment, an antibody contains at least one (for example, from one to about ten, preferably 2, 3, 4, 5, 6, 7 or 8) amino acid insertions, deletions and/or substitutions in CDR-regions of parental antibody. This application defines the identity or homology regarding the sequence of a variant antibody as the percentage of amino acid residues in a variant antibody sequence which are identical to residues in parental antibody after aligning the sequences and, if needed, cutting in order to achieve the maximum percentage identical sequence. A variant antibody keeps its ability to bind the same antigen or, preferably, epitope as that with which the parental antibody binds, or, preferably, exhibits at least one property or biological activity exceeding that of the parental antibody. For example, the antibody preferably has a more strong affinity, longer half-life, lower $IC_{50}$ or increased ability to inhibit the antigen activity, compared to parental antibody. A variant antibody of particular interest in the present application is an antibody showing at least 2-fold, preferably at least 5-fold, 10-fold or 20-fold increased activity when compared to parental antibody.

"Parental" antibody, as used herein, refers to an antibody encoded with amino acid sequence that is used to produce a variant. Parental antibody can have a framework sequence originating from Lama glama, and preferably the frame sequence is of completely or substantially human origin. Parental antibody can be from llama, chimeric, humanized or human.

Antibodies of the invention can be prepared using various engineering techniques including recombinant methods such as shuffling of DNA of various origins.

As used herein, the term "specifically binds" refers to such a situation in that one party involved in the process of specific binding does not significantly bind molecules other than its specific binding partner (partners). This term also applies if, for example, an antigen-binding site of the antibody according to the invention is specific for particular epitope which is carried by a number of antigens; in this case the specific antibody with an antigen-binding site will be able to bind specifically with various epitope-carrying antigens. Thus, the monoclonal antibody according to the invention specifically binds to human IL-17 (IL-17A), while it does not specifically bind human IL-17B, IL-17C, IL-17D, IL-17E and IL-17F.

As used herein, the term "epitope" refers to the molecule part that can be recognized by and bind an antibody via one or several antigen-binding sites of an antibody. Epitopes often comprise the chemically surface active groups of molecules such as amino acids or sugar side chains, and have specific 3-D structural characteristics and specific charge characteristics. "Inhibiting epitope" and/or "neutralizing epitope" means an epitope that, as in the context of an intact antigen molecule and binding an antibody specific to said epitope, causes in vivo or in vitro loss or reduction of activity of the molecule or organism that contains the molecule.

As used herein, the term "epitope" also refers to polypeptide fragment having antigenic and/or immunogenic activity in animals, preferably in mammals such as mice and humans. The term "antigenic epitope", as used herein, is a polypeptide fragment which can specifically bind the antibody and can be detected by any technique well known from the prior art (for example, by means of the standard immunoassay). Antigen epitopes are not necessary immunogenic, but they can have immunogenicity. "Immunogenic epitope", as used herein, is defined as a polypeptide fragment that evokes an antibody response in animals, as determined by any method of the prior art. "Nonlinear epitope" or "conformational epitope" contains nonadjacent polypeptides (amino acids) within the antigen protein which binds with epitope-specific antibody.

The terms "Biological property", "biological characteristics", "activity" and "biological activity" referring to an antibody according to the invention are interchangeable, as used herein, and include but not limited to: epitope/antigen affinity and specificity; ability to neutralize or be an antagonist to IL-17 in vivo or in vitro; $IC_{50}$; antibody stability and in vivo immunogenicity of the antibody. Other biological properties or antibody characteristics identified from the prior art include, for example, the cross-reactivity (i.e. reaction with non-human homologs of the target peptide or with other proteins or targets) and ability to retain high levels of protein expression in mammal cells. Aforementioned properties or characteristics may be observed, measured or evaluated using the procedures recognized in the prior art, including but not limited to ELISA, competitive ELISA, BIACORE surface plasmon resonance or KINEXA, neutralization assay in vitro or in vivo without limitation, receptor binding, production and/or release of cytokine or growth factor, signal transduction and immune histochemical study of tissue sections obtained from various sources including humans, primates or any other source.

As used herein, the terms "inhibit" or "neutralize" regarding to antibody activity according to the invention shall mean the ability to resist, block, prevent, restrict, slow down, interrupt, destroy, stop, reduce or reverse significantly, for example, the development or severity of inhibition subject, including but not limited to biological activity (such as activity of IL-17) or property, disease or condition. Binding of the antibody according to the invention with IL-17 causes inhibition or neutralization of IL-17 activity preferably of at least 20, 30, 40, 50, 60, 70, 80, 90, 95% or higher.

The term "patient", as used herein, refers to mammals including but not limited to mice, monkeys, humans, livestock mammals, sports mammals and pet mammals; preferably the term applies to humans. In a certain embodiment the patient, preferably mammal, preferably human, is additionally characterized by IL-17A-mediated disease, disorder, or condition which can be improved by reduction of IL-17 biological activity.

The term "vector" refers to nucleic acid molecules that can transport another nucleic acid to which it is linked, including but not limited to plasmids and viral vectors. Certain vectors can autonomously replicate in host cells to which they were introduced, while other vectors can integrate into host cell genome and replicate together with the host genome. Moreover, some vectors can mediate the expression of genes to which they are functionally bound. In this application such vectors are called "recombinant expression vectors" (or "expression vectors"); exemplary vectors are well known from the prior art.

As used herein, the terms "cell", "host cell", "cell line", "cell culture" and "producer cell line" are interchangeable and refer to an individual cell or cell culture that is a recipient of any separated polynucleotide according to the invention or any recombinant vector (recombinant vectors) which contain the sequence encoding HCVR, LCVR or a monoclonal antibody according to the invention. Host cells involve generations obtained from an individual host cell; generations may not necessary be completely identical (regarding the morphology or full DNA complement) to original host cell due to natural, accidental or intended mutations and/or variations. A host cell includes cells that were transformed, transduced or infected with recombinant vector, or a monoclonal antibody that expresses a polynucleotide according to the invention or its heavy or light chain. Host cell that contains a recombinant vector according to the invention (either incorporated into host chromosomes or not) can also be called "recombinant host cell". Preferable host cells to be used in the invention are CHO cells (for example, ATCC CRL-9096), NS0 cells, SP2/0 cells, COS cells (ATCC, for example, CRL-1650, CRL-1651) and HeLa (ATCC CCL-2). Additional host cells to be used in the invention include plant cells, yeast cells, other mammalian cells and prokaryotic cells.

The term "IL-17A-mediated disease or disorder" includes diseases or disorders that are associated with abnormal body/tissue levels of IL-17. Such disease or disorder can be either infection/inflammation or of an autoimmune nature and may be selected from rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroadenitis, asthma, allergic disorders, psoriasis, dermatitis, systemic sclerosis, graft-versus-host disease, graft rejection, acute or chronic immune disease associated with organ grafting, sarcoidosis, atherosclerosis, disseminated intravascular coagulation, Kawasaki disease, Graves' disease, nephrotic syndrome, chronic fatigue syndrome, Wegener's disease, Henoch-Schonlein purpura, microscopic polyangiitis with renal involvement, chronic active hepatitis, uveitis, septic shock, toxic shock syndrome, sepsis syndrome, cachexia, infections, invasions, acquired immune deficiency syndrome, acute transverse myelitis, Huntington chorea, Parkinson disease, Alzheimer disease, stroke, primary biliary cirrhosis, hemolytic anemia, malignancies, heart failure, myocardial infarction, Addison disease, polyglandular autoimmune syndrome type I and type II, Schmidt's syndrome, acute respiratory distress syndrome, alopecia, alopecia areata, seronegative arthropathy, arthropathy, Reiter's syndrome, psoriatic arthropathy, arthropathy associated with ulcerative colitis, enteropathic synovitis, arthropathy associated with *Chlamydia, Yersinia* and *Salmonella*, spondyloarthropathy, atheromatosis disease/coronary sclerosis, atopic allergy, autoimmune bullous disease, pemphigus, pemphigus foliaceus, pemphigoid, linear IgA diseases, autoimmune hemolytic anemia, Coombs positive hemolytic anemia, acquired pernicious anemia, juvenile pernicious anemia, Myalgic encephalomyelitis/chronic fatigue syndrome, chronic active hepatic inflammation, cranial giant arteritis, primary sclerosing hepatitis, cryptogenic autoimmune hepatitis, acquired immune deficiency syndrome (AIDS), AIDS-associated diseases, hepatitis B, hepatitis C, common variable immunodeficiency (common variable hypogammaglobulinemia), dilated cardiomyopathy, female sterility, ovarian insufficiency, Premature ovarian failure, pulmonary fibrosis, cryptogenic fibrosing alveolitis, post inflammatory interstitial lung pathologies, interstitial pneumonitis, connective tissue disease associated with interstitial lung disease, mixed connective tissue disease associated with interstitial lung disease, systemic scleroderma associated with interstitial lung disease, rheumatoid arthritis associated with interstitial lung disease, systemic lupus erythematosus associated with lung disease, dermatomyositis/polymyositis associated with lung disease, Sjogren disease associated with lung disease, ankylosing spondylitis associated with lung disease, diffuse pulmonary vasculitis, hemosiderosis associated with lung disease, drug-induced interstitial lung disease, fibrosis, radiation-induced fibrosis, obliterating bronchiolitis, chronic eosinophilic pneumonia, lung disease with lymphocyte infiltration, post infectious interstitial lung pathologies, gouty arthritis, autoimmune hepatitis, autoimmune hepatitis type I (classic autoimmune or lupoid hepatitis), autoimmune hepatitis type II (associated with anti-LKM antibody), autoimmune hypoglycemia, type B insulin resistance with acanthokeratodermia, hypoparathyroidism, acute graft-associated immune disease, chronic graft-associated immune disease, osteoarthrosis, primary sclerosing cholangitis, type I psoriasis, type II psoriasis, idiopathic leukopenia, autoimmune neutropenia, NOS-kidney diseases, glomerulonephritis, microscopic renal polyangiitis, Lyme disease, discoid lupus erythematosus, idiopathic of NOS-male sterility, antisperm immunity, multiple sclerosis (all types), sympathetic ophthalmia, pulmonary hypertension secondary to connective tissue disease, Goodpasture syndrome, pulmonary manifestations of polyarteritis nodosa, acute rheumatic fever, rheumatoid spondylitis, Still's disease, systemic scleroderma, Sjogren's Syndrome, Takayasu disease/arthritis, autoimmune thrombocytopenia, idiopathic thrombocytopenia, autoimmune thyroid disorders, hyperthyroid, autoimmune hypothyroidism (Hashimoto disease), atrophic autoimmune hypothyroidism, primary myxedema, phacogenic uveitis, primary vasculitis, vitiligo, acute hepatic disease, chronic hepatic disease, alcoholic cirrhosis, alcohol-induced liver damage, cholestasis, idiosyncratic hepatic disease, drug-induced hepatitis, nonalcoholic steatohepatitis, allergies and asthma, group B streptococcal infection (GBS), mental disorders (including depressions and schizophrenia), Th1- and Th2-mediated disease, acute and chronic pain (various forms), malignancies such as lung cancer, breast cancer, stomach cancer, bladder cancer, colorectal cancer, pancreatic cancer, ovarian cancer, prostate cancer and hematopoietic malignancies (leukemia and lymphomas), abetalipoproteinaemia, acrocyanosis, acute and chronic infections and infestations, acute leukemia, acute lymphoblastic leukemia, acute myeloid leukemia, acute or chronic bacterial infection, acute pancreatitis, acute renal failure, adenocarcinoma, atrial ectopics, AIDS dementia complex, alcohol-induced hepatitis, allergic conjunctivitis, allergic contact dermatitis, allergic rhinitis, allograft rejection, alpha-I antitrypsin deficiency, lateral amyotrophic sclerosis, anemia, angina, anterior horn cell degeneration, anti-CD3 therapy, antiphospholipid syndrome, hypersensitivity reactions against receptors, aortic and peripheral aneurysms, aortic dissection, arterial hypertension, coronary sclerosis, arteriovenous fistula, ataxia, atrial fibrillation (constant or paroxysmal), atrial flutter, atrioventricular block, B-cell lymphoma, bone graft rejection, bone marrow transplant (BMT) rejection, bundle branch block, Burkitt lymphoma, burns, cardiac arrythmia, myocardial stunning syndrome, cardiac tumor, cardiomyopathy, inflammatory response to bypass, cartilage graft rejection, brain cortex degeneration, cerebellar disorder, chaotic or multifocal atrial tachycardia, chemotherapy-induced disorders, chronic myelocytic leukemia (CML), chronic alcohol addiction, chronic inflammatory pathologies, chronic lymphatic leukemia (CLL), chronic obstructive pulmonary disease, chronic salicylate intoxication, rectocolic carcinoma, congestive cardiac failure, conjunctivitis, contact dermatitis, pulmonary heart, coronary artery disease, Creutzfeldt-Jakob Disease, culture-negative sepsis, cystic fibrosis, cytokine therapy-induced disorders, boxer's encephalopathy, demyelinating disease, dengue hemorrhagic fever, dermatitis, dermatological conditions, diabetes, diabetes mellitus, diabetes-related atherosclerotic vascular disease, diffuse Lewy body disease, congestive dilated cardiomyopathy, basal ganglia disease, Down's syndrome in middle age, motor disorders induced by CNS dopamine blockers, drug sensitivity, eczema, encephalomyelitis, endocarditis, endocrinopathy, epiglottiditis, Epstein-Barr viral infection, erythralgia, extrapyramidal and cerebellar symptoms, familial hemophagocytic lymphohistiocytosis, fetal thymus graft rejection, Friedreich's ataxia, peripheral artery disease, fungal sepsis, gas phlegmon, gastric ulcer, glomerulonephritis, any organ or tissue graft rejection, gram negative sepsis, gram positive sepsis, granulomas due to intracellular organisms, hairy-cell leukemia, Hallervorden-Spatz disease, Hashimoto's thyroiditis, hay fever, heart transplant rejection, hemochromatosis, hemodialysis, hemolytic uremic syndrome/thrombotic thrombocytopenic purpura, bleeding, hepatitis (A), bundle branch arrhythmia, HIV-infections/HIV-neuropathies, Hodgkin disease, hyperkinetic motor disorders, hypersensitivity reactions, hypersensitivity-associated pneumonitis, hypertension, hypokinetic motor disorders, examination of hypothalamo-pituitary-adrenal axis, idiopathic Addison's disease, idiopathic pulmonary fibrosis, antibody-mediated cytotoxicity, asthenia, infantile muscular atrophy, aortal inflammation, influenza virus A, exposure to ionizing radiation, iridocyclitis/uveitis/optic neuritis, ischaemia/reperfusion-induced disorders, ischaemic stroke, juvenile rheumatoid arthritis, juvenile spinal muscular atrophy, Kaposi's sarcoma, renal transplant rejection, legionellosis, leishmaniasis, leprosy, corticospinal damage, lipoedema, liver transplant rejection, lymphoedema, malaria, malignant lymphoma, malignant histiocytosis, malignant melanoma, meningitis, meningococcemia, metabolic/idiopathic diseases, migraine, multiple system mitochondrial disorders, mixed connective-tissue disease, monoclonal gammapathy, multiple myeloma, multiple system degeneration (Mencel Dejerine-Thomas Shi-Drager and Machado-Joseph), myasthenia gravis, intracellular *Mycobacterium avium, Mycobacterium tuberculosis*, myelodysplastic syndrome, myocardial infarction, myocardial ischemic disease, nasopharyngeal cancer, neonatal chronic lung disease, nephritis, nephrotic, neurodegenerative disorders, neurogenic muscular atrophy I, neutropenic fever, non-Hodgkin's lymphomas, abdominal aortic branch occlusion, arterial occlusive disease, OKT3® treatment, orchitis/epididymitis, orchitis/vasectomy reversal operations, organomegaly, osteoporosis, pancreatic graft rejection, pancreatic carcinoma, paraneoplastic disease/tumor-related hypercalcemia, parathyroid graft rejection, pelvic inflammatory disease, perennial rhinitis, pericardial disease, peripheral atherosclerosis (atherlosclerotic) disease, peripheral vascular disease, peritonitis, pernicious anemia, *Pneumocystis carinii* pneumonia, POEMS syndrome (polyneuropathy, organomegaly, endocrinopathy, monoclonal plasma-proliferative disorder and skin changes), postperfusion syndrome, pump head syndrome, post-cardiotomy post-infarction syndrome, preeclampsia, progressive supranuclear paralysis, primary pulmonary hypertension, radiation therapy, Raynaud's phenomenon and disease, Raynoud's disease, Refsum's disease, regular narrow QRS tachycardia, renal vascular hypertension, reperfusion injury, restrictive cardiomyopathy, sarcoma, scleroderma disease, senile chorea, Dementia with Lewy bodies, seronegative arthritis, shock, sickle cell disease, skin allograft rejection, skin changes, small intestinal graft rejection, solid tumors, specific arrhythmias, spinal ataxia, spinocerebellar degradations, streptococcal myositis, cerebellar structural damage, subacute sclerosing panencephalitis, syncope, cardiovascular syphilis, systemic anaphylaxis, a comprehensive systemic inflammatory response syndrome, systemic-onset juvenile rheumatoid arthritis, T cells or FAB ALL, telangiectasia, thrombosis obliterans, thrombocytopenia, toxicity, grafting, trauma/bleeding, hypersensitivity reactions type III, hypersensitivity reactions type IV, unstable angina, uremia, urinary sepsis, urticaria, valvular heart disease, varicose veins, vasculitis, venous diseases, venous thrombosis, ventricular fibrillation, viral and fungal infections, vital encephalitis/aseptic meningitis, vital hemophagocytic syndrome, Wernicke-Korsakoff syndrome, Wilson's disease, heterograft rejection for any organ or tissue, acute coronary syndrome, acute idiopathic polyneuritis, acute inflammatory demyelinating radicular neuropathy, acute ischemia, adult-onset Stills disease, alopecia areata, anaphylaxis, antiphospholipid antibody syndrome, aplastic anemia, coronary sclerosis, atopic eczema, atopic dermatitis, autoimmune dermatitis, autoimmune disorder associated with streptococcus infection, autoimmune enteropathy, autoimmune hearing loss, autoimmune lymphoproliferative syndrome (ALPS), autoimmune myocarditis, autoimmune premature ovarian failure, blepharitis, bronchiectasis, bullous pemphigoid, cardiovascular disease, catastrophic antiphospholipid syndrome, celiac disease, cervical spondylosis, chronic ischemia, cicatrical pemphigoid, clinically isolated syndrome (cis) with the risk for multiple sclerosis, conjunctivitis, childhood-onset mental disorders, chronic obstructive pulmonary disease (COPD), dacryocystitis, dermatomyositis, diabetic retinopathy, diabetes mellitus, herniated disk, prolapse of intervertebral disc, drug-induced immune haemolytic anaemia, endocarditis, endometreosis, entophthalmia, episcleritis, erythema multiform, severe erythema multiform, gestational pemphigoid, Guillain-Barre syndrome (GBS), hay fever, Hughes syndrome, idiopathic Parkinson's disease, idiopathic interstitial pneumonia, IgE-mediated allergy, autoimmune hemolytic anemia, inclusion body myositis, infectious ocular inflammatory disease, inflammatory demyelinating disease, inflammatory heart disease, inflammatory kidney disease, idiopathic pulmonary fibrosis/ usual interstitial pneumonia, iritis, keratitis, keratoconjunctivitis sicca, Kussmaul disease or Kussmaul-Meier Disease, Landry palsy, Langerhans' cell histiocytosis, marbled skin, macular degeneration, microscopic polyangiitis, Bechterew disease, motor neuron disease, mucosal pemphigoid, multiple organ failure, myasthenia gravis, spinal cord dysplasia syndrome, myocarditis, nerve root disorders, neuropathy, non-A, non-B hepatitis, optic neuritis, osteolysis, ovarian cancer, oligoarticular JIA, peripheral arterial occlusive disease, peripheral vascular disease, peripheral artery disease (PAD), phlebitis, polyarteritis nodosa, polychondritis, polymyalgia rheumatica, poliosis, polyarticular juvenile idiopathic arthritis, multiple endocrine deficiency, polymyositis, polymyalgia rheumatica (PMR), post pump syndrome, primary parkinsonism, prostate and rectal cancer and hematopoietic malignancies (leukemia and lymphoma), prostatitis, pure red-cell aplasia, primary adrenal insufficiency, relapsing neuromyelitis optica, restenosis, rheumatic heart disease, SAPHO (synovitis, acne, pustulosis, hyperostosis and osteitis), sclerodermia, secondary amyloidosis, shock lung, scleritis, ischias, secondary adrenal insufficiency, silicon-associated connective tissue disease, Sneddon-Wilkinson disease, ankylosing spondylitis, Stevens-Johnson syndrome, systemic inflammation response syndrome, cranial arteritis, Toxoplasma rhinitis, toxic epidermal necrolysis, transverse myelitis, TRAPS (tumor necrosis factor receptor-associated periodic syndrome), allergic reactions type I, diabetes type II, urticaria, usual interstitial pneumonia, vasculitis, vernal conjunctivitis, viral retinitis, Vogt-Koyanagi-Harada syndrome (VKH syndrome), wet macular degeneration, wound healing, and *Yersinia*- or *Salmonella*-associated arthropathy.

Description of Antibodies

The present invention proposes antibodies or fragments thereof that specifically bind to IL-17A; variable domain ($V_H$) of the heavy chain comprises 3 hypervariable regions HCDR1, HCDR2 and HCDR3:

Hypervariable region HCDR1 includes SEQ NO: 1;
Hypervariable region HCDR2 includes SEQ ID: NO 2, and
Hypervariable region HCDR3 includes SEQ ID NO: 3,
Variable domain ($V_L$) comprises 3 hypervariable regions LCDR1, LCDR2 and LCDR3:
Hypervariable region LCDR1 includes SEQ ID NO: 4,
Hypervariable region LCDR2 includes SEQ ID NO: 5 and
Hypervariable region LCDR3 includes SEQ ID NO: 6.

Preferable embodiments of the invention involve a monoclonal antibody or fragment thereof comprising variable domains of the heavy (VH) and light (VL) chains, wherein the said antibody or fragment thereof comprises:

```
HCDR1 of
                                      (SEQ ID NO: 7)
F-T-F-S-N-Y-A-M-S;

HCDR2 of
                                      (SEQ ID NO: 8)
R-I-E-G-G-I-S-S-T-Y;

HCDR3 of
                                      (SEQ ID NO: 9)
C-A-V-N-Y-Y-G-M-Y-Y;
```

And variable region VL of the light chain comprises:

```
LCDR1 of
                                      (SEQ ID NO: 10)
T-G-T-S-E-D-V-G-F-G-N-Y;

LCDR2 of
                                      (SEQ ID NO: 11)
R-V-N-T-R-P-S;

LCDR3 of
                                      (SEQ ID NO: 12)
C-S-S-Y-K-A-G-G-T-Y.
```

Another preferable embodiment of the invention involves a monoclonal antibody or fragment thereof that specifically binds to human IL-17A, or an antibody fragment comprising variable domains of the heavy chain (VH) and the light chain (VL), where the said antibody or its active fragment contains at least one variable domain of:

a) The heavy chain variable domain (VH) of SEQ ID NO: 13.
b) The light chain variable domain (VL) of SEQ ID NO: 14.

the antibody of the invention can comprise a heavy chain sequence identical to SEQ ID NO: 15. Another embodiment of the invention is an antibody comprising a light chain with amino acid sequence identical to SEQ ID NO: 16.

The antibodies of the invention can include additional mutations M252Y/S254T/T256E, N434W, N434A, N434F, H433K/N434F/Y436H, H433K/N434F/Y436H+M252Y/S254T/T256E, T307A/E380A/N434A, T250Q/M428L. Aforementioned substitutions do not result in the loss of antibody's ability to bind to IL-17A, but they can result in reducing of ADCC (antibody-dependent cell-mediated cytotoxicity) or increasing the affinity or other biological properties of the antibody.

Antibodies of the invention possess improved biological properties, especially better inhibiting activity (IC50) in respect of IL-17A, as well as enhanced aggregate stability.

Also, the invention provides a DNA construct encoding the antibodies claimed, and an expression vector comprising said DNA construct for production of antibodies of the invention.

Moreover, the invention suggests a cell line comprising an expression vector with DNA as described above. This cell line can be used for production of antibodies of the invention.

Pharmaceutical Composition

An antibody of the invention can be involved into a pharmaceutical composition suitable for administration in patients (please see Example 14). Antibodies of the invention can be administered separately or in combination with a pharmaceutically acceptable carrier, vehicle and/or diluent, in single or multiple doses. Pharmaceutical compositions for administration were developed to meet the mode of administration chosen; and pharmaceutically acceptable diluents, carriers and/or vehicles such as dispersing agents, buffers, surface-active agents, preservatives, solubilizing agents, isotonic agents, stabilizers, etc. are used properly (please see Example 14). The said compositions were developed in accordance with the standard methods specified in, for example, Remington, The Science and Practice of Pharmacy, 19th Edition, Gennaro, Ed., Mack Publishing Co., Easton, Pa. 1995, which describes the common techniques for formulation production.

A pharmaceutical composition comprising an anti-IL-17 monoclonal antibody of the invention can be administered to a patient who has a risk of a pathology or a pathology as described herein, using the standard administration techniques including oral, intravenous, intraperitoneal, subcutaneous, pulmonary, transdermal, intramuscular, nasal, buccal, sublingual or via suppositories.

A pharmaceutical composition of the invention preferably contains or is a therapeutically effective amount of an antibody of the invention. "Therapeutic effective amount" refers to an amount effective in doses and for time periods needed to achieve the desired therapeutic result. Therapeutic effective amount of an antibody may vary depending on such parameters as disease state, age, subject's gender and weight, and ability of an antibody or its fragment to induce the desired reaction in the patient. Also the therapeutic effective amount is an amount for which the therapeutic benefit of an antibody exceeds the toxic or adverse effects. "Prophylactic effective amount" refers to an amount effective in doses and during time periods needed to achieve the desired prophylactic result. Since prophylactic doses are used in subjects prior to the disease or on an early stage of the disease, typically the prophylactic effective amount can be less than the therapeutic effective amount.

Therapeutically effective or prophylactic effective amount is at least a minimum dose, but less than the toxic dose of an active ingredient, required to assure the therapeutic benefit for the patient. At the same time, a therapeutically effective amount of an antibody of the invention is an amount that reduces the activity of IL-17 (for example, IL-17R binding) in mammals, preferably humans, in which the presence of IL-17 causes or promotes any adverse pathological effects, or if the reduction of IL-17 results in a therapeutic benefit in mammals, preferably humans.

The route of administration of an antibody of the invention can be oral, parenteral, inhalation or local. Preferably antibodies of the invention can be involved in a composition acceptable for parenteral administration. The term "parenteral" as used herein includes intravenous, intramuscular, subcutaneous, rectal, vaginal or intraperitoneal administration. Intravenous, intraperitoneal or subcutaneous injections are preferred routs of administration. Acceptable pharmaceutical carriers for such injections are well known from the prior art.

As described in appropriate guidelines, pharmaceutical compositions shall be sterile and stable upon the production and storage in a container, which is providing, for example, in hermetically sealed vials (for examples, ampoules) or syringes. Thus, pharmaceutical compositions can be subjected to filtration sterilization after preparing the composition, or can be made microbiologically suitable by any other method. A typical composition for an intravenous infusion can include 250-1000 ml of fluid such as sterile Ringer's solution, normal saline, dextrose solution or Hank's salt solution, and a therapeutically effective dose (for example, 1-100 mg/ml or higher) of an antibody concentrate. Doses may vary depending on disease type and severity. It is well known from the state of medical art that doses for a certain patient depend on multiple factors including patient's sizes, body surface area, age, specific compound to be administered, gender, duration and route of administration, general health state and simultaneously administered medications. A typical dose can be, for example, in a range of 0.001-1000 µg; however, doses lower and higher than this illustrative range are anticipated, especially given the above mentioned parameters. Daily parenteral dosing regimen may be from 0.1 µg/kg to 100 µg/kg of body weight, preferably from 0.3 µg/kg to 10 µg/kg, and further preferably from 1 µg/kg to 1 µg/kg, further preferably from 0.5 to 10 µg/kg of body weight per day. The treatment process can be monitored by periodical assessment of patient's health state. For repeated administration for several days or longer, depending on patient's condition, the treatment is repeated until the desired response or disease control. However, another dosing regimens not described herein can also be applied. Appropriate dose may be administered by single bolus or multiple bolus dosing, or by means of a continuous infusion of an antibody depending upon a desired pharmacokinetic breakdown.

Said assumed properties of an antibody largely depend on physician's decision. The intended effect is a key factor for choosing a proper dose and regimen. Parameters considered herein include a certain disease to be treated, a certain mammal to receive the treatment, clinical condition of a certain patient, disorder cause, administration site, a certain antibody type, route of administration, mode of administration and other factors well known from the medical arts.

Therapeutic agents according to the invention can be frozen or lyophilized and recovered in sterile carrier prior to the administration. Freeze-drying and recovery can result in some loss of antibody's activity. Doses can be adjusted to compensate this loss. In general, formulation pH from 6 to 8 are preferable.

Articles of Manufacture

In another embodiment, an article of manufacture is provided containing materials useful for the treatment or prevention of the disorders described above.

The article of manufacture comprises a container with an antibody-containing pharmaceutical composition, and a label or package insert. Suitable containers include, for example, vials, ampoules, syringes and analytical tubes. Containers may be formed from a variety of materials such as glass or plastic. The container comprises a composition of the invention which is effective for treating Il-17A-mediated disease or disorder and can have a sterile access port (for example the container may be an intravenous solution bag or a vial having a stopper pierceable by a hypodermic injection needle). Anti-IL-17 antibody of the invention is an active ingredient of the composition. The label or package insert indicates that the composition is used for treating the condition desired. Moreover, the article of manufacture may comprise a second container with a pharmaceutically acceptable buffer such as phosphate-buffered saline, Ringer's solution and dextrose solution. It can further include other materials desirable from a commercial and user standpoint, including other buffers, diluents, filters, needles, syringes and package inserts.

The examples below are presented in illustrative purposes only and are not intended to limit the scope of the present invention.

EXAMPLES

Example 1

Producing Recombinant Antigens and Antibodies in Suspension Mammal Cell Culture

Antibodies and antigens were generated in established cell line obtained from Chinese hamster ovary cells (CHO-K1) according to published protocols [Biotechnol Bioeng. 2005 Sep. 20; 91(6):670-677, Liao Metal., 2004; Biotechnol Lett. 2006 June; 28(11):843-848; Biotechnol Bioeng. 2003 Nov. 5; 84(3):332-342]. Cells constitutively expressing the gene of EBNA1 protein (Epstein-Barr virus nuclear antigen 1) were used. Suspension culture was conducted in flasks on orbital shaker using serum-free media from Life Technologies Corporation and in accordance with manufacturer's guidelines. For transient expression cells in a concentration of $2*10^6$/ml were transfected by means of linear polyethyleneimine (PEI MAX, Polysciences). DNA/PEI ratio was 1:3-1:10. In 5-7 days after transfection, cell culture was centrifuged under 2000 g for 20 min and filtered through 0.22 µm filter. Target proteins from culture liquid were isolated by affine HPLC.

Figure 1:
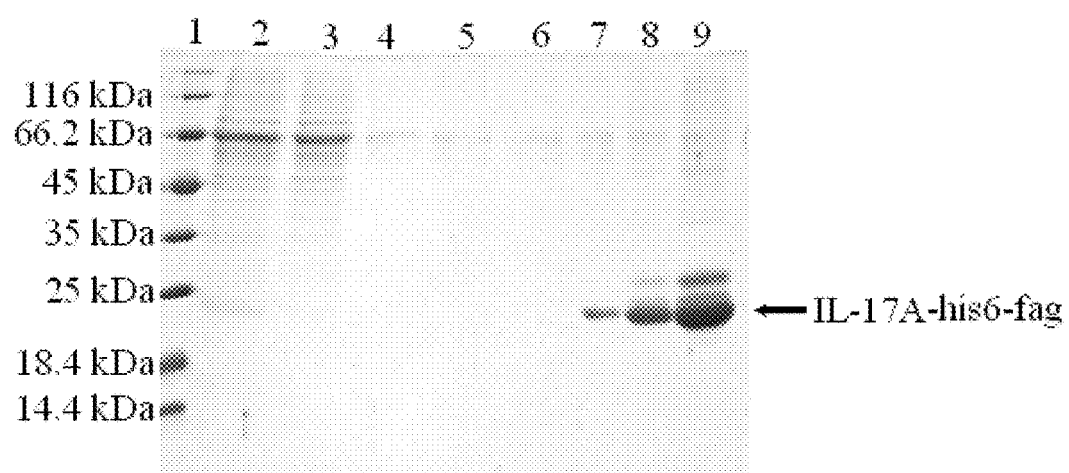
FIG. 1 shows a Phoregram of IL-17A protein solution, wherein:
Lane 1 is $9^{10}$ 0.25 µg+β-MEU;
Lane 2 is $9^{10}$ 0.5 µg+β-ME;
Lane 3 is $9^{10}$ 1 µg+β-ME;
Lane 4 is - - - ;
Lane 5 is Enzyme-unstained marker;
Lane 6 is Medium before application on IMACBioRad;
Lane 7 is Medium after application on IMACBioRad;
Lane 8 is Washing 1; and
Lane 9 is Washing 2.

Recombinant IL-17A protein containing 6 His amino acids in C-terminal region was isolated and purified from culture liquid on Profinity IMAC Ni-charged resin (Bio-Rad). Prior to purification procedures, $NiCl_2$ was added to culture liquid to a concentration of 1 mM. Then 5 ml of Profinity IMAC Ni-charged was added to culture liquid and mixed on a shaker for 1 h at room temperature. Sorbent was transferred to 5 ml Thermo scientific Polypropylene columns and washed with 5 column volumes of PBS to remove non-specifically bound components. Bound antigen was eluted with 0.3 M imidazole (pH 8) and 150 mM NaCl. Then the protein was dialyzed into PBS (pH 7.4) by means of SnakeSkin Dialysis Tubing technique, filtered (0.22 μm), transferred into tubes and stored at −70° C. Purity of the protein obtained was evaluated by SDS-PAGE (FIG. 1).

Figure 2:
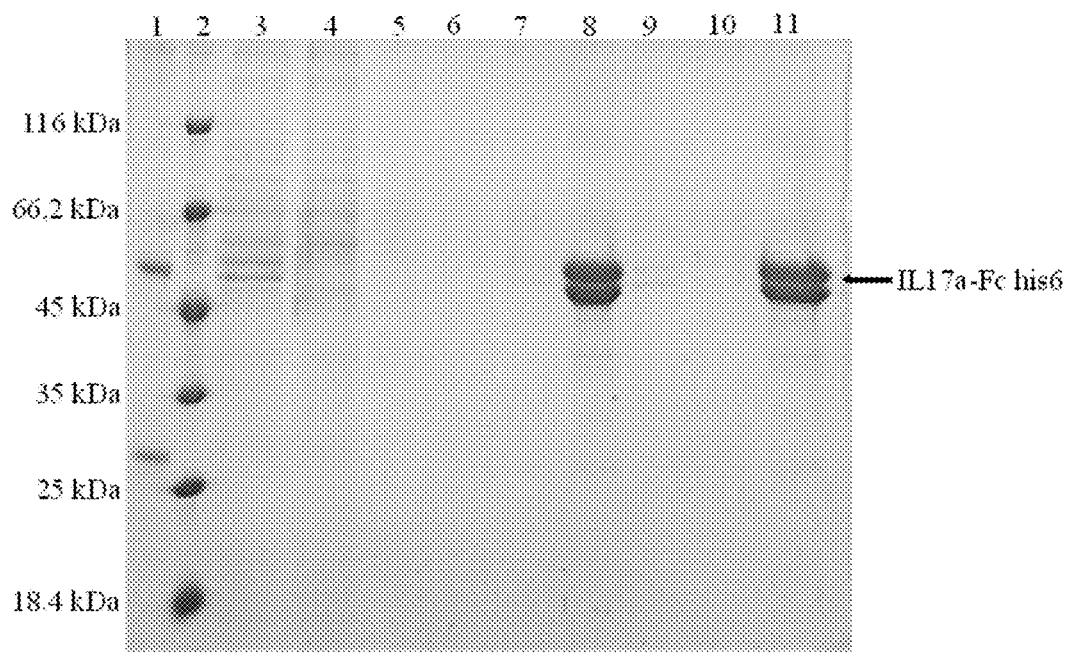
FIG. 2 shows a Phoregram IL-17A-Fc protein solution, wherein:
Lane 1 is 910 murine-IgG 1 µg;
Lane 2 is Enzyme-unstained marker;
Lane 3 is Medium before application 10 µL;
Lane 4 is Medium after application 10 µL;
Lane 5 is Washing with PBS-Tween 10 µL;
Lane 6 is Washing with PBS 10 µL;
Lane 7 is Elution the first 10 µL;
Lane 8 is Elution 12 ml 10 µL;
Lane 9 is Elution 12 ml 10 µL;
Lane 10 is Washing of sorbent pH 2.5 10 µL; and
Lane 11 is IL-17-Fc after dialysis 10 µL.

Recombinant IL-17A-Fc protein was isolated and purified from cell culture on Protein A column for affine HPLC. Cleared culture liquid was passed through 5 ml HiTrap rProtein A Sepharose FF column (GE Healthcare) equilibrated with PBS (pH 7.4). Then the column was washed with 5 volumes of PBS to remove unbound components. Bound antigen was eluted with 0.1 M glycine buffer pH 3. The principal protein elution peak was collected and brought to neutral pH with 1 M Tris-buffer (pH 8). All stages were conducted under 11-cm/h flow rate. Isolated protein was then dialyzed into PBS (pH 7.4) using SnakeSkin Dialysis Tubing technique, filtered (0.22 μm), transferred into tubes and stored at −70° C. Purity of the protein obtained was evaluated by SDS-PAGE (FIG. 2).

Figure 3A:
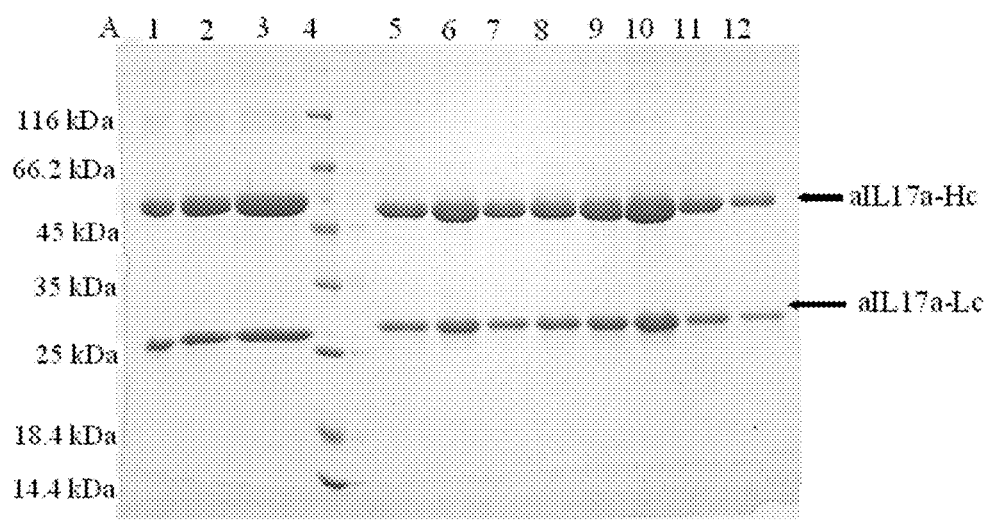
FIGS. 3A and 3B.
Figure 3B:
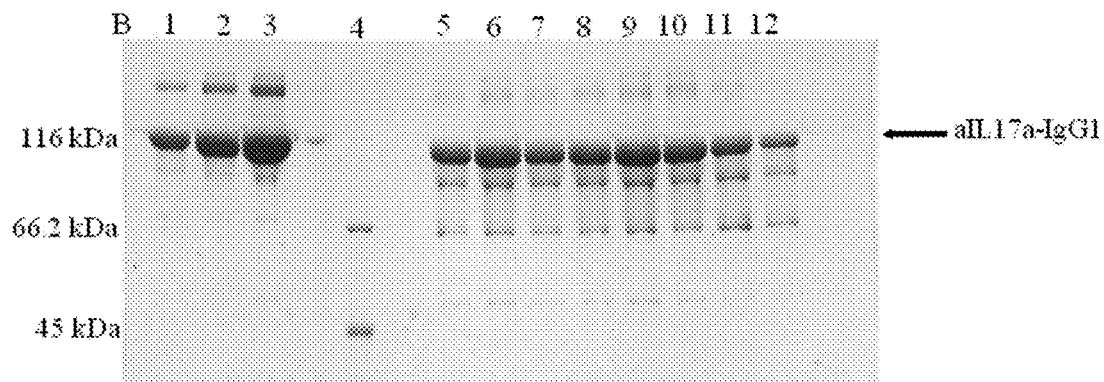

IgG1 antibodies were purified on 1 ml Hi Trap rProteinA FF column (GE Healthcare) in accordance with the procedure aforementioned for IL-17A-Fc. Purity of the protein obtained was evaluated by SDS-PAGE (FIGS. 3A and 3B).

Example 2

Llama Immunization with Human IL-17A and Generation of Fab-Library of Phage-Displayed Llama Antibodies Lama Glama was immunized 5 times in succession by means of subcutaneous administration of antigen material mixed with an equal volume of complete (first injection) or incomplete Freund's adjuvant. A mixture of recombinant proteins (0.2 mg of each protein per injection) one of which was human IL-17A (Kit from R&D Systems) was used as an antigen. Second injection (immunization stage) was performed 3 weeks after the first one; three more immunizations were performed with a 2-week interval. Blood samples (50 ml) were collected 5 after each injection starting from the third one.

Blood was 2-fold diluted with PBS containing 1 mM EDTA. Then 35 ml of diluted blood were layered over 15 ml of Histopaque®-1077 medium (Sigma, density of 1.077 g/ml) and centrifuged for 20 min under 800 g. Mononuclear cells (lymphocytes and monocytes) were selected from plasma/Histopaque medium interphase zone and washed with PBS containing 1 mM EDTA.

Total RNA from mononuclear llama cells was isolated using RNeasy Mini Kit in accordance with the protocol (QIAGEN). RNA concentration assay was performed using Nanovue (GE Healthcare); the quality of isolated RNA was tested by means of 1.5% agarose gel electrophoresis.

Reverse transcription reaction was conducted using MMLV RT kit (Evrogen) according to the recommended protocol with MMuLV reverse transcriptase and random hexamer primers.

Figure 4:
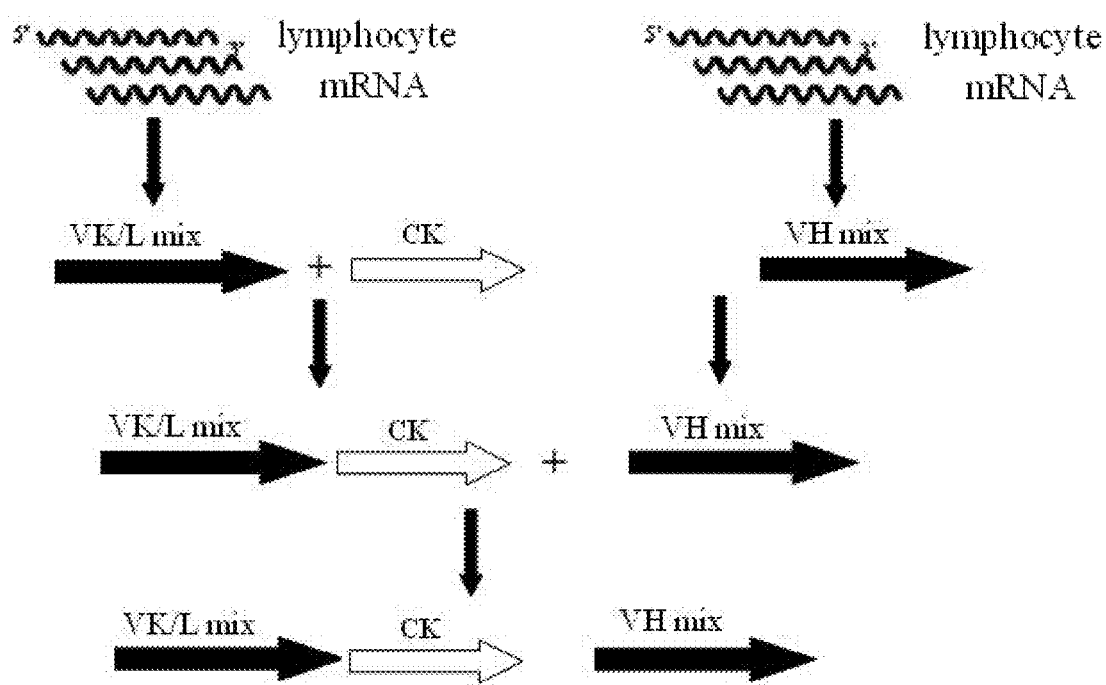
FIG. 4 shows a Flow-chart for the synthesis of llama combinatorial antibody Fab library.
Figure 5:
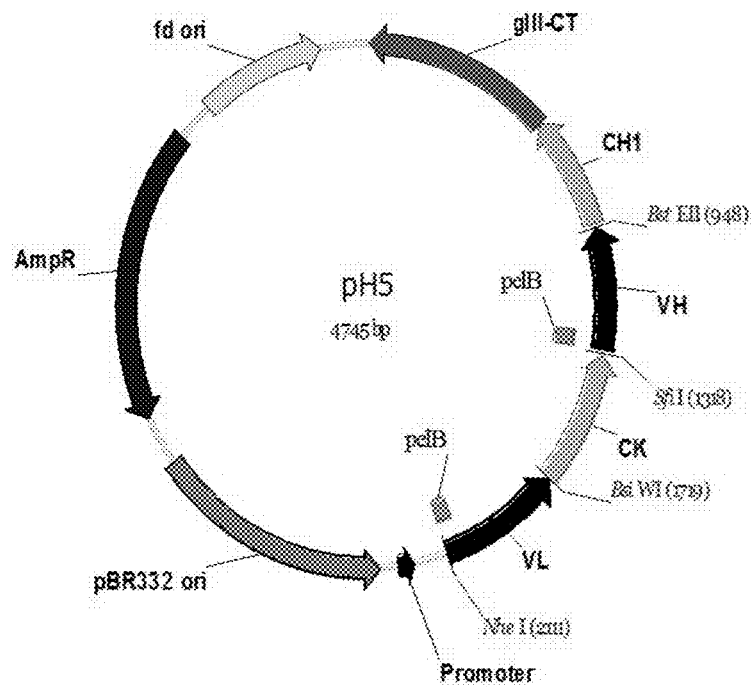
FIG. 5 shows a Phagemid for cloning of phage display Fab libraries.

Reverse transcription products were used as a matrix in a two-stage polymerase chain reaction to obtain the genes of variant domains flanked with restriction sites; reaction was performed using oligonucleotide kit and protocols by [J Biol Chem. 1999 Jun. 25; 274(26): 18218-30; WO 2010/001251]. Further, genes encoding variable domains of the light and heavy chains were put together in one fragment by means of sequential reactions of restriction, ligation and amplification as shown in FIG. 4. Heavy chain genes were attached separately to kappa and lambda light chain genes. In this case the estimated count of matrix molecules in all reactions was no less than $10^{11}$. The DNA product obtained (VL-CK-VH) was treated with NheI/Eco91I restriction enzymes and ligated into original phagemid pH 5. Phagemid structure is presented in FIG. 5. Ligation products were transformed into SS320 electrocompetent cells prepared in accordance with protocols [Methods Enzymol. 2000; 328: 333-63]. The repertoire of constructed kappa and lambda Fab libraries was $5.1*10^8$ and $3.7*10^8$, respectively. The product of naïve phage-display library was prepared in accordance with the earlier described procedure [J Mol Biol. 1991 Dec. 5; 222(3):581-97].

Example 3

Selection of Fab-Libraries of Phage-Display Antibodies

Specific anti-IL17A phage-display Fab-antibodies were selected from a phage Fab-display library using a recombinant human IL-17A (a kit from R&D Systems); a series of selection cycles was performed as described in J Biol Chem. 1999 Jun. 25; 274(26): 18218-30; Nat Biotechnol. 1996 March; 14(3):309-14; J Mol Biol. 1991 Dec. 5; 222(3): 581-97. To perform the selection process by panning method, human IL-17A in 50 mM carbonate buffer (pH 9.5) was adsorbed overnight at 4° C. on the surface of HighSorb tubes (Nunc). Further, tubes were washed with PBS (pH 7.4) and then blocked with solution containing PBS (pH 7.4)—fat-free milk (0.5% weight/volume) for 1 hour. Then, 2-4 ml of phage solution ($10^{12}$ phage particles per ml) in PBS (pH 7.4)—fat free milk (0.5% w/vol) were transferred to the tube with the antigen and the system was incubated for 1 h under stirring. Unbound phages were removed by a series of washing cycles with PBS (pH 7.4)—Tween 20 (0.1% vol./vol.). The number of washing cycles was increased from the first round to the third one—20-30-40 times, respectively. Phage particles that remained bound were eluted with 100 mM Gly-HCl solution (pH 2.5) during 15 min under stirring, and then neutralized with 1 M TRIS-HCl (pH 7.6). *E. coli* TG1 bacteria were infected with phages obtained; further phages were isolated and used in the next cycle.

Example 4

Generation of Chimeric Phage-Display Antibody Fab-Libraries

Total B-lymphocyte RNA from blood collected from 550 subjects was isolated using RNeasy Mini Kit in accordance with the protocol (QIAGEN). RNA concentration assay was performed using Nanovue kit (GE Healthcare), while the quality of isolated RNA was tested by 1.5% agarose gel electrophoresis.

Reverse transcription reaction was performed using MMLV RT kit (Evrogen) in accordance with the recommended protocol with MMuLV reverse transcriptase and random hexamer primers.

Figure 6:
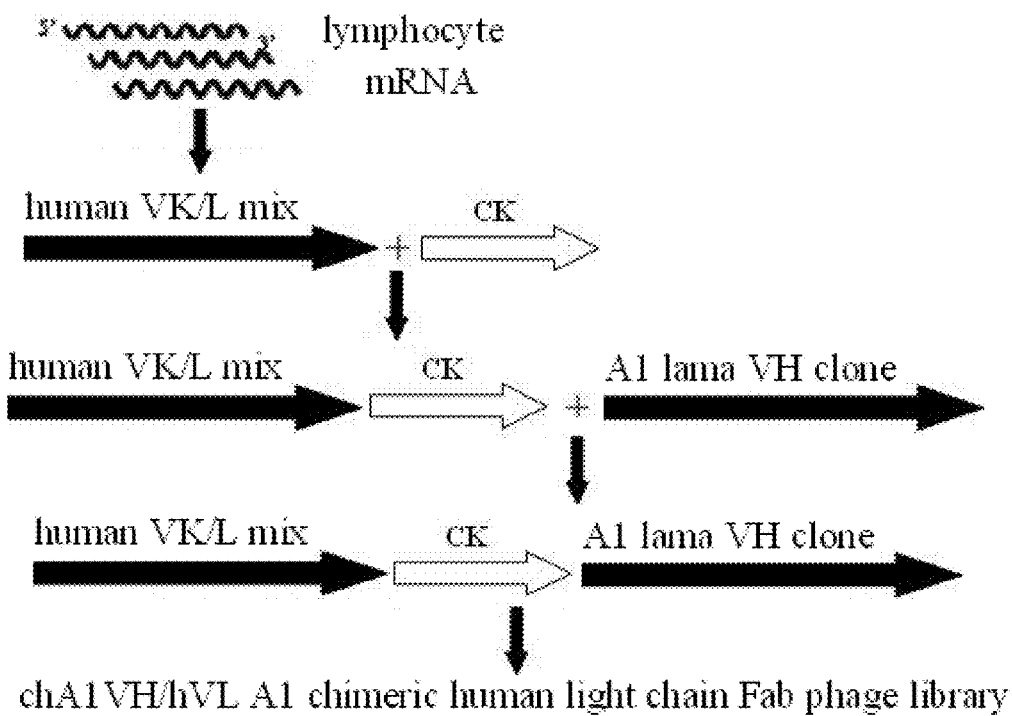
FIG. 6 shows a Flow-chart for the synthesis of hybrid combinatorial antibody Fab libraries.
Figure 7:
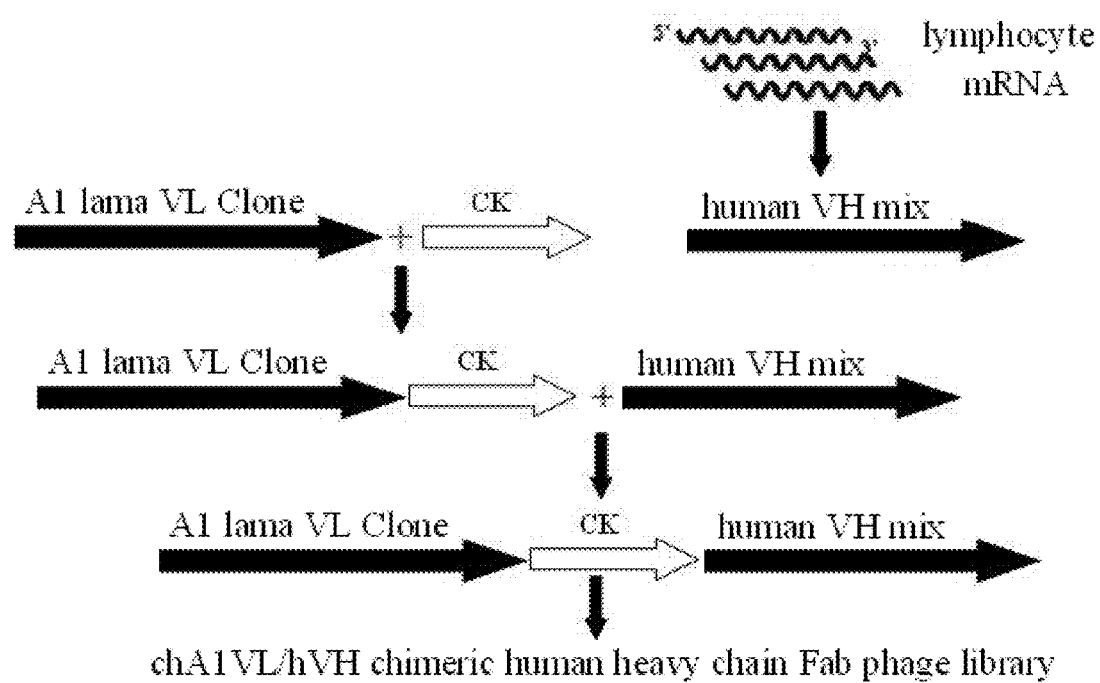
FIG. 7 shows a Flow-chart for the synthesis of hybrid combinatorial antibody Fab libraries.

Reverse transcription products were used as a matrix for a two-stage polymerase chain reaction to obtain the variable domain genes flanked with restriction sites; reaction was performed using an oligonucleotide kit and protocols from J Biol Chem. 1999 Jun. 25; 274(26): 18218-30. Chimeric Fab which are specific against IL-17A were engineered using the technology described in an international publication WO93/06213 and based on an original phagemid pH5 described above. For this purpose, genes of human donor light chain variable domains and genes of llama antibody A1 heavy chain variable domain were connected into a single fragment by means of successive reactions of restriction, ligation and amplification, as shown on a chart (FIG. 6). Similarly, genes of llama antibody A1 light chain variable domain, genes of human donor heavy chain variable domains and genes of llama antibody A1 heavy chain variable domain were connected into a single fragment by means of successive reactions of restriction, ligation and amplification, as shown on FIG. 7. The estimated number of molecules of the matrix of human variable domain genes in all reactions was no less than $10^{12}$. Obtained DNA preparation VL-CK-VH was treated with restriction enzymes NheI/Eco91I and ligated into an original phagemid pH5. Ligation products were transformed into electrocompetent SS320 cells prepared according to protocols described in [Methods Enzymol. 2000; 328: 333-63.]. The repertoire of chimeric Fab-library chA1VH/hVL based on the heavy chain of A1 clone and mixed kappa and lambda human chains included $2.8*10^9$ transformants. The repertoire of chimeric Fab-libraries chA1VL/hVH based on the light chain of A1 clone and human heavy chains included $1.1*10^{10}$ transformants. Phage preparations from chimeric Fab-libraries were prepared in accordance with the procedure described in [J Mol Biol. 1991 Dec. 5; 222(3): 581-97].

Selection of obtained phage-display chimeric Fab-libraries was performed under the conditions similar to those described above (refer to the selection of phage-display Fab-libraries).

After the second round of selection on IL-17A, both libraries demonstrated significant enrichment. Resulting pooled clones from enriched chimeric Fab-libraries were used as a source for combinations of human variable domain genes VH and VK/VL specific against IL-17A.

Example 5

Engineering of Phage Display Human Fab-Phage Anti-IL-17A Antibody Libraries

Figure 8:
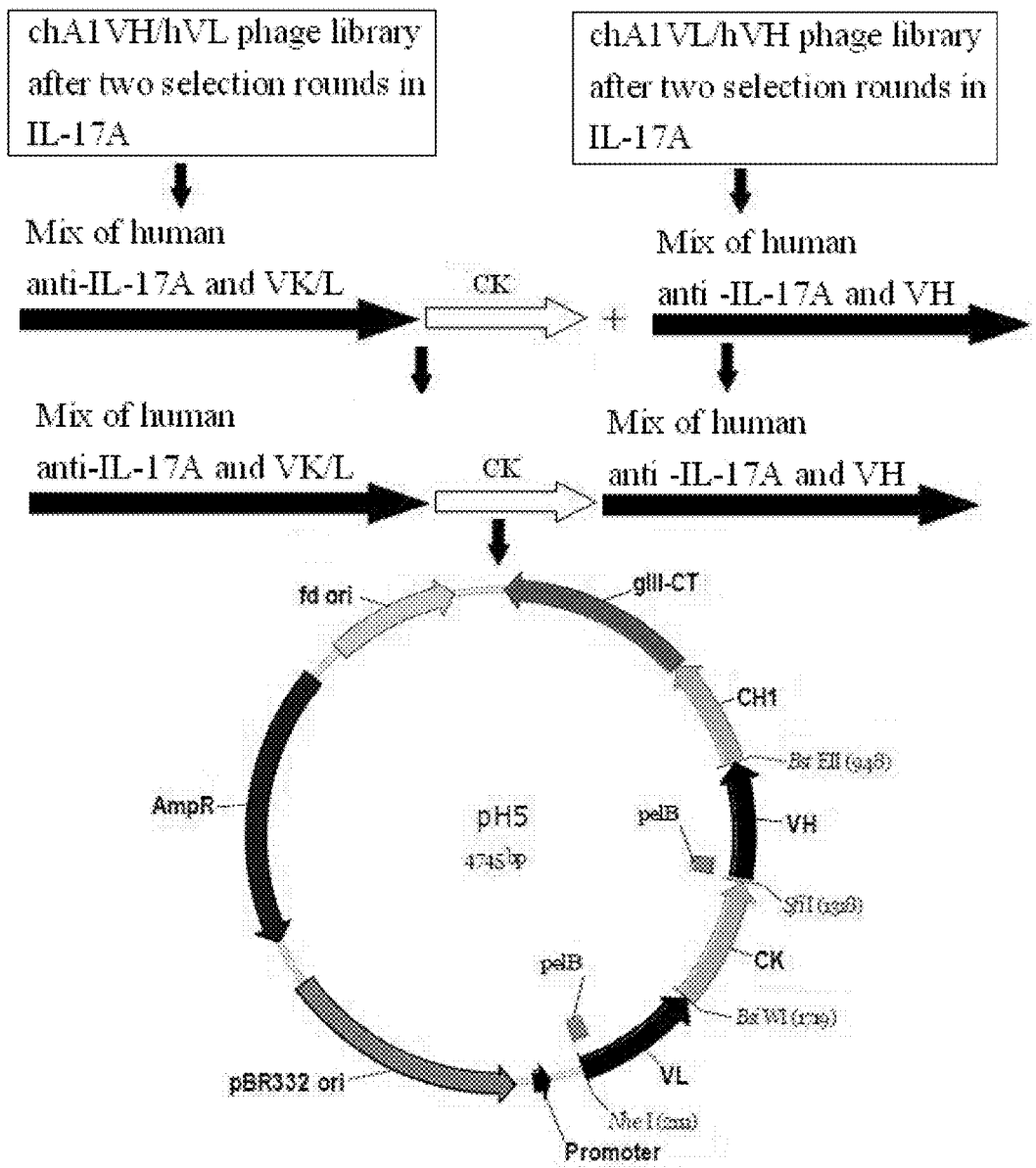
FIG. 8 shows a Combination of variable domain pools.

To create human Fab phage antibodies against IL-17A, pooled clones from enriched chimeric Fab-libraries were used as a source for integration of genes of human VH and VK/VL variable domains specific against IL-17A. In this regard the genes of human light chains were amplified with specific primers from chA1VH/hVL library enriched after a second round, while the genes of human heavy chains were amplified with specific primers from chA1VL/hVH library enriched after a second round. Both pools of human chain variable domains were successively combined by means of restriction with SfiI restriction enzyme, ligation and amplification in accordance with the pattern shown in FIG. 8. Obtained VL-CK-VH DNA product was treated with NheI/Eco91I restriction enzymes and ligated into the original phagemid pH5. Ligation products were transformed into electrocompetent SS320 cells prepared according to [Methods Enzymol. 2000; 328: 333-63]. Repertoire of Fab-library of human heavy and light chains was $8.6*10^8$. Preparations of phage-displayed chimeric Fab libraries were obtained in accordance with the earlier described procedure [Mol Biol. 1991 Dec. 5; 222(3): 581-97].

Selection of obtained phage chimeric Fab-libraries was performed under the same conditions as described for the selection of phage Fab-libraries.

After a second round of selection on IL-17A, ELISA performed for a polyclonal phage product showed significant enrichment. A resulting pooled clone enriched with human Fab and specific against IL-17A was re-cloned into an expression plasmid.

Example 6A

Analysis of Fab Specific Binding with Human IL-17A-Fc

ELISA is used to measure the binding of studied Fab-fragments with human IL-17A. Fab with published AIN457 sequence (Novartis) was used as a positive control. ELISA plate wells (Nunc ImmunoMaxisorp) were coated with 50 µl (0.5 µg/ml in 1× coating carbonate buffer) IL-17A-Fc, hermetically closed and incubated overnight at 4° C. All further stages were conducted in accordance with the standard ELISA protocols with a high-performance systems such as GenetixQ-pix2xt (Molecular Devices) and Tecan Freedom EVO 200 (Tecan). Non-specific binding was blocked by adding the blocking buffer BB (200 µl 0.5% fat-free milk in PBS). Plates were incubated on a shaker for 1 h at room temperature. After washing with PBS-Tween, each cell was coated with 50 µl of test Fab-containing cell supernatant mixed with the equal volume of BB. Plates were incubated on a shaker for 1 hour at room temperature; further each plate well was 5 times washed with PBS-Tween buffer. After washing, each well was coated (50 µl/well) with anti-human Fab HRP-conjugated secondary antibody (Pierce-ThermoScientific) in PBS-Tween (1:5000). Plates were transferred to rotation shaker (50 min at room temperature) and then 5 times washed with PBS-Tween buffer as described above. Colorimetric signal was obtained by adding TMB (100 µl/well) until saturated (average of 3-5 min); further color development was blocked by adding the stop solution (100 µl/well, 10% sulfuric acid). Absorbance was measured at 450 nm using an appropriate Tecan-Sunrise plate reader (Tecan). Antibody binding was proportional to the signal produced.

Figure 9:
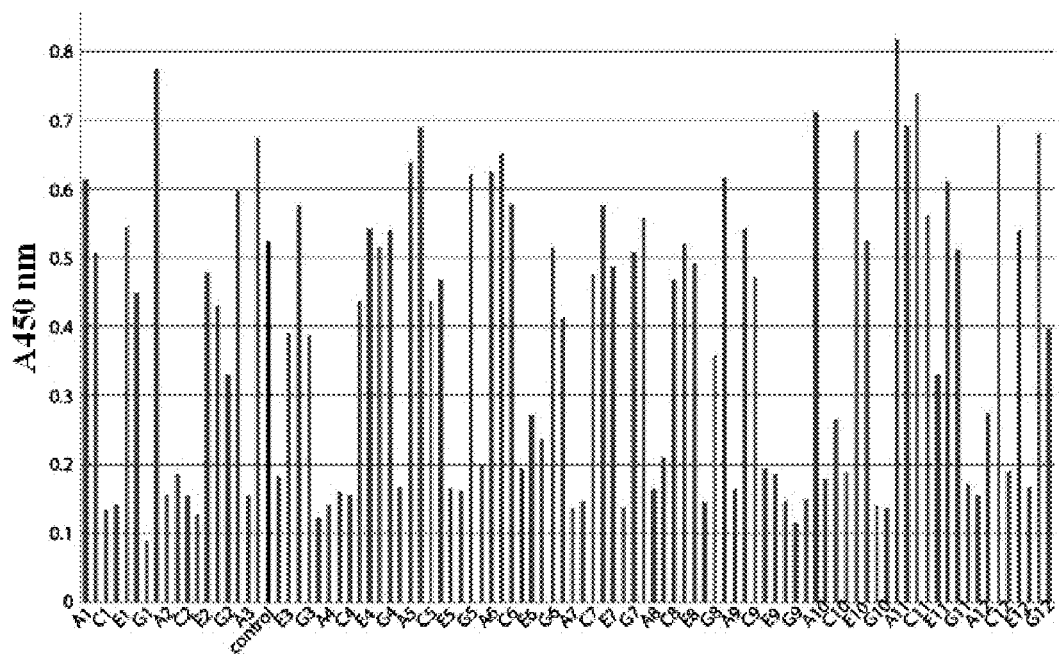
FIG. 9 shows a ELISA screening of Fab specific against human IL-17.

For example, ELISA results obtained from one plate with llama Fab after a second selection round are shown in FIG. 9. The histogram represents a number of positive clones with a signal over or under the control Fab (AIN457) (marked in red color) or those that never bound to an immobilized antigen (0.1-0.2 relative unit).

Example 6B

Competitive ELISA of Blocking the Interaction of IL17A Ligand and IL17R Receptor Competitive ELISA technique was used to test the antagonistic capacity of previously selected Fab specific against human IL-17A-Fc. Fab with published AIN457 sequence (Novartis) was used as a positive antagonist control. Wells of ELISA plate (Nunc Immuno Maxisorp) were covered with 50 µl/well IL-17RA-Fc receptor (R&D Systems; 1 µg/ml solution in 1× coating carbonate buffer) and incubated overnight at 4° C. All further stages were performed in accordance with standard ELISA protocols with a high-performance systems such as GenetixQ-pix2xt (Molecular Devices) and Tecan Freedom EVO 200 (Tecan). Non-specific binding was blocked by adding the blocking buffer BB (200 µl 0.5% fat-free milk in PBS). Plates were incubated for 1 hour on a shaker at room temperature.

In parallel, 50 µl of test Fab-containing cell supernatant in non-binding 96-well plate was mixed with 50 µl of IL-17A-His6-Flag (0.4 µg/ml in 1% milk diluted with PBS-Tween). The plate was incubated for 1 hour at 37° C. on a shaker under 500 rpm.

After the plate containing IL-17RA-Fc receptor was washed of BB solution, it was coated with the reaction mixture of Fab and IL-17A-His6-Flag in the amount of 90 µl per well. Plates were incubated under shaking for 45 min at room temperature. And each well was 5 times washed with PBS-Tween buffer. Further 50 µl/well of 1 µg/ml anti-FLAG murine M2 antibody (Sigma) were added and plates were incubated for 45 min at room temperature. After incubation, each plate well was 5 times washed with PBS-Tween, and each well was coated with 50 µl of antimurine-IgG HRP-conjugated secondary antibody (Pierce-Thermo-Scientific) 1:5000 diluted with PBS-Tween. Plates were incubated on rotation shaker for 45 min at room temperature and 5 times washed with PBS-Tween, as mentioned above. Colorimetric signal was obtained by adding TMB (100

μl/well) until saturated (average of 3-5 min); further color development was blocked by adding the stop solution (100 μl/well, 10% sulfuric acid). Absorbance was measured at 450 nm using an appropriate Tecan-Sunrise plate reader (Tecan). Antibody binding was proportional to the signal produced.

Figure 10:
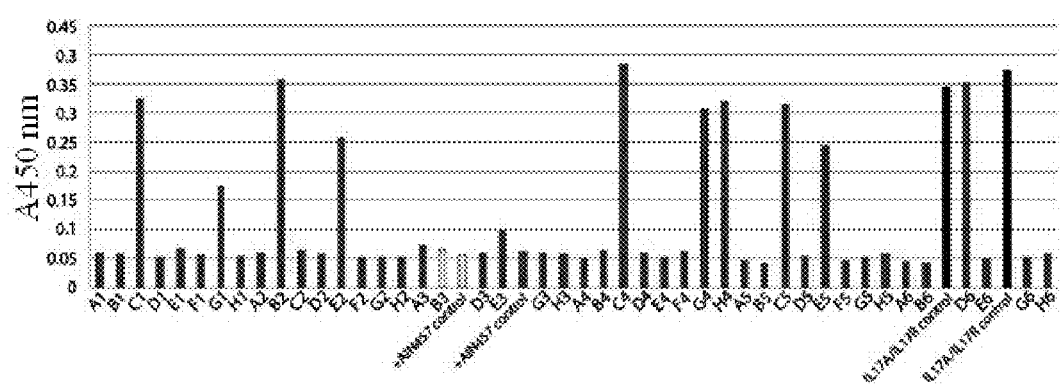
FIG. 10 shows a Competitive ELISA screening of Fab-candidates blocking IL-17A/IL-17R interaction.

For example, ELISA results obtained from one plate with llama Fab after a second selection round are shown in FIG. 10. The histogram represents a number of positive clones with a signal comparable (0.05-0.1 relative units) to that of control Fab (AIN457, marked in red color) or clones that never blocked IL-17A/IL-17R interaction (signal similar to that obtained with controls of direct ligand-receptor interaction, marked in dark blue).

Example 7

Comparative Koff-Screening of Human Anti-IL-17A Fab Candidates

Koff screening is performed for anti-17A Fab-candidates. Koff-screening is carried out using Pall Forte Bio Octet Red 96 system. Anti-FABCH1 biosensors were rehydrated for 30 min in a working buffer comprising 10 mM PBS (pH 7.2-7.4), 0.1% Tween-20 and 0.1% BSA. 10× working buffer was added to test samples of *E. coli* supernatants up to 1× final concentration. Then anti-FABCH1 biosensors were steeped into *E-coli* supernatants containing Fab-fragments of candidate antibodies and incubated for 12 hours at a temperature of 4° C. Sensors coated with Fab-fragments were transferred to wells with working buffer, and a baseline was registered (60 sec). Then sensors were transferred to wells with analyte solution (IL-17A, 30 μg/ml) to achieve the antigen-antibody association (300 sec). After that, sensors were returned into wells with working buffer for further dissociation (300 sec). Used sensors were subject to regeneration after each test: they were three times placed into regenerating buffer (Gly-HCl, pH 1.7) and then were applicable for use in further experiments. The curves obtained were analyzed using Octet Data Analysis (version 7.0) according to the standard procedure with 1:1 interaction model.

Figure 11:
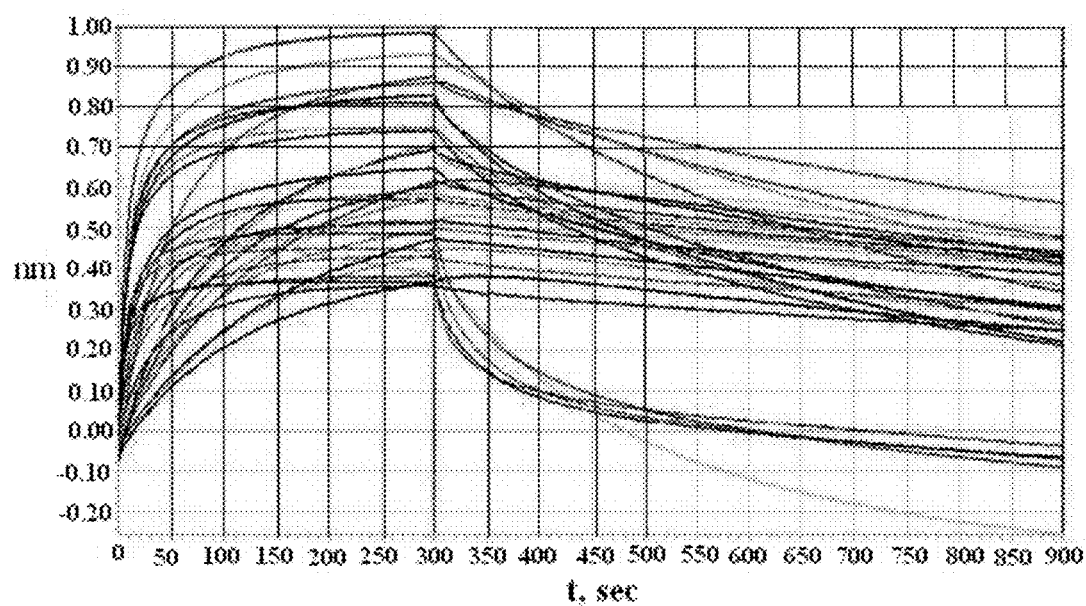
FIG. 11 shows a graph indicating the results of koff-screening of human anti-IL-17A Fab candidates.

Results obtained for koff-screening of anti-IL-17A Fab human candidates are shown in FIG. 11.

Example 8

Scanning Mutagenesis of Variable Domain CDRs and Selection of High-Affinity Candidates Mutations to individual positions of candidate's CDRs were inserted by means of NNK randomization technique [Appl Environ Microbiol. 2006 February; 72(2):1141-7; MAbs. 2012 May-June; 4(3):341-8] using Q5® Site-Directed Mutagenesis Kit (from NEB) in accordance with the protocol. A1-Fab-pLL plasmid was used as a matrix. PCR products were fractioned on low-melting agarose and purified on appropriate columns After ligation, DNA was transformed to *E. coli* expression strain BL21gold (Stratagene). The individual clones obtained were then gained by Fab expression in 96-well plates, as described above. Supernatants containing mutant Fab arms were analyzed by ELIZA under the conditions described above and using the high-performance Genetix Q-pix2xt and Tecan Freedom EVO200 systems. The concentration of immobilized IL-17A was 0.2 μg/ml. Bound Fab arms were stained with 1:5000 diluted Goat anti-Human IgG (Fab')2 (HRP) conjugate (Pierce) and TMB+H2O2/H2SO4 dye; absorption was measured at 450 nm wave length.

Results obtained by scanning mutagenesis are presented in Table 1. The Table shows within-CDR substitutions that correspond to ≤30% reduction of mutant Fab/human Il-17A binding signal when compared to the wild type sequence. Thus, such individual mutants or any combination thereof are the invention.

TABLE 1

Scanning mutagenesis

| Mutation position | Positive amino acids in mutants |
|---|---|
| HCDR3 | |
| V99 | R, N, A, I |
| N100 | E, L, M, S, T, V |
| Y101 | — |
| Y102 | F, V |
| G103 | S |
| M104 | A, F, L, P, Y |
| Y105 | F, H, I, M, S, W |
| Y106 | A, I, N, R, S, V |
| HCDR2 | |
| R50 | G, I, L, M, S |
| D52 | D, E |
| G53 | M |
| G54 | L, R, V |
| I55 | L |
| S57 | L, R, T, W |
| S58 | T, Y |
| T59 | L, R, S, W |
| Y60 | T, L, K |
| HCDR1 | |
| N31 | D, K, L, M, P, T |
| Y32 | F |
| A33 | G, M, N, S, T, V |
| M34 | I |
| S35 | G, N, T |
| LCDR3 | |
| A91 | S |
| S92 | G, T |
| Y93 | A, F, I |
| R94 | K |
| A95 | S |
| G96 | F |
| G97 | H |
| T98 | — |
| Y99 | I, L, W |
| LCDR2 | |
| R52 | E, L, M |
| V53 | L, S |
| N54 | G |
| T55 | I, K, L, M, R, W |
| LCDR1 | |
| E27 | N, R |
| D28 | S, T |
| V29 | L, R |
| G30 | V |
| F31 | L, S, T, V, Y |
| G32 | L, V |
| N33 | P, R, S |
| Y34 | A, L, W |

Thus, the screening was performed for BCD085 antibody CDR amino acid positions that are tolerant to amino acid substitutions. It was demonstrated that the present panel of amino acid substitutions does not significantly change the antibody binding with human IL-17A. The said substitution panel can be used to improve various candidate properties.

Example 9

Engineering of a Stable Cell Line, Producing and Purification of an Antibody

A stable cell line producing BCD085 antibodies was obtained by transfecting the parental suspension CHO-S cell line with vector constructs that comprised the optimum ratio of light and heavy antibody chains. High level clonal lineages (over 100 mg/L) were obtained using ClonePix robotic platform (Molecular Devices). Productivity of selected clones was analyzed by Biomek FX robotics (Beckman Coulter) and Octet RED96 analytical system (Pall Life Sciences). Producer was cultured in serum-free media containing no animal-derived proteins. BCD085 for preclinical studies was accumulated in HyClone single-use bioreactor (Thermoscientific) of 200 L operating volume.

Figure 12:
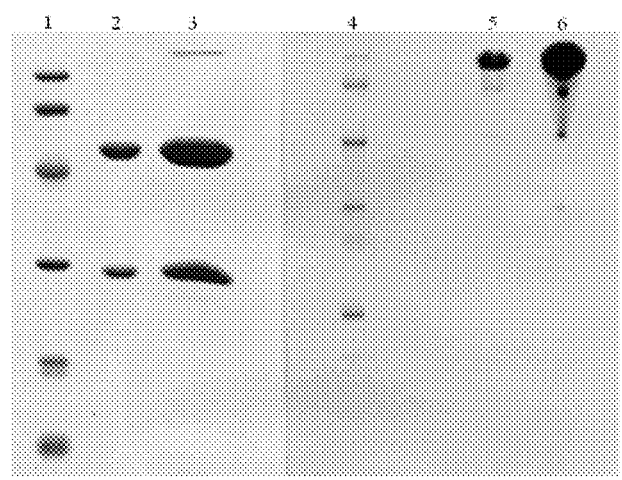
FIG. 12 shows a Electrophoregram of BCD085 solution, wherein
Lane 1 is Enzyme-unstained Marker;
Lane 2 is BCD085, 10 µg+βME;
Lane 3 is BCD085, 40 µg+βME;
Lane 4 is Enzyme-unstained Marker;
Lane 5 is BCD085, 10 µg−βME; and
Lane 6 is BCD085, 40 µg−βME.

The culture liquid was filtered through Zeta Plus Maximizer 4516701 60M02 depth filter equipped with a peristaltic pump. Primary purification of the antibody was performed on MabSelect Protein A affinity medium (GE Healthcare Life Sciences). After clarification by depth filtration, the culture liquid was applied to the sorbent equilibrated with a buffer comprising 50 mM HCl-Tris (pH 7.5) and 150 mM NaCl. The sorbent then was washed with equilibration buffer followed by low-conductivity HCl-Tris. Protein elution was conducted using Gly-HCl buffer (pH 3.5). Collected eluate was exposed to acidic pH for 30 min for the purpose of viral inactivation, and then neutralized with 1M Tris-base to pH 6.8. When brought to proper pH, the protein solution was filtered on STERICUP systems with MilliporeExpressPlus® 0.22 μm membrane (PVDF). Final purification to remove DNA, host-cell proteins and released affine sorbent's ligand was performed by flowing the protein solution through prepared Q Sepharose FF (GE HealthCare), pH 7.0, under the low conductivity (<2 msec/cm$^2$). Purified protein was then subject to virus-removing filtration on UltiporVF filter (PALL), concentrating and diafiltration against the final buffer containing His/HisHCl (pH 6.0-6.5), Tween-80 and trehalose. The protein concentration was 50 mg/ml and higher. Purification of the protein obtained were evaluated by SDS-PAGE (FIG. 12).

Figure 13:
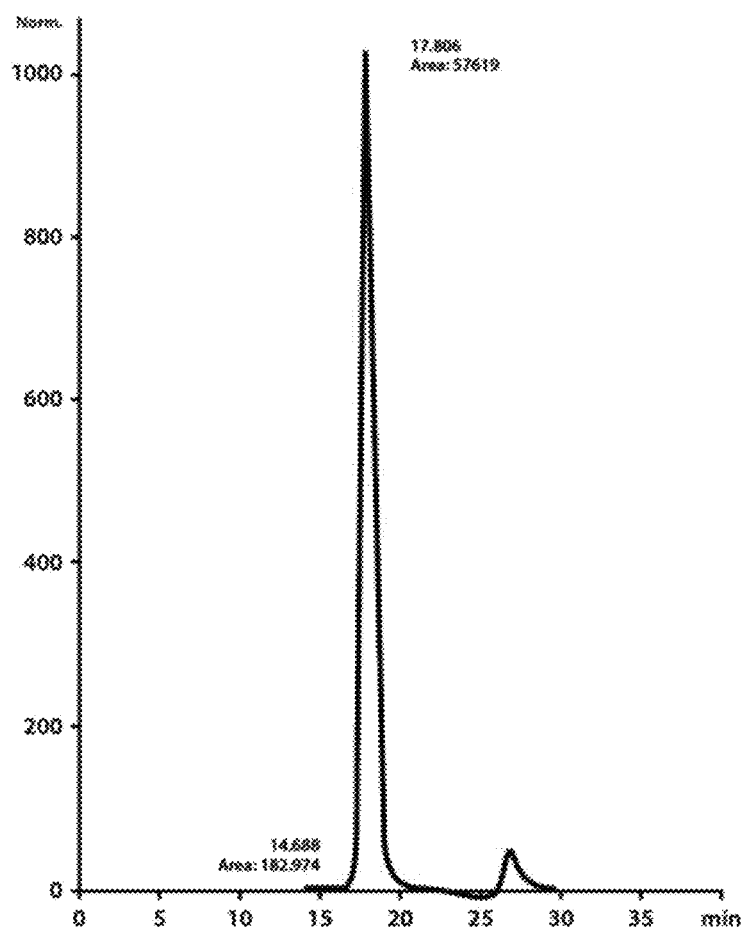
FIG. 13 shows a size-exclusion HPLC profile of purified BCD085.

Additionally, the aggregate composition of the product was assessed by size-exclusion HPLC (FIG. 13).

Chromatographic analysis was performed using Agilent 1100 system and Tosoh TSK-Gel G3000SWXL column 7.8 mm×30 cm (Cat. No. 08541) with Tosoh TSKgel Guard SWXL pre-column 6.0 mm×4.0 cm (particles of 7 μm, Cat. No. 08543). Isocratic elution with mobile phase containing 50 mM sodium phosphate buffer and 0.3 M NaCl (pH 7.0) was performed under 0.5 ml/min flow rate with the detection at 214 nm and 280 nm wave lengths. Antibody samples were diluted with PBS (pH 7.5) to a concentration of ~1 mg/ml. Injection volume was 10 μl. Gel filtration standard mixture (Bio-Rad, Cat. No. 151-1901) was used to calibrate the column prior to the test.

Figure 14:
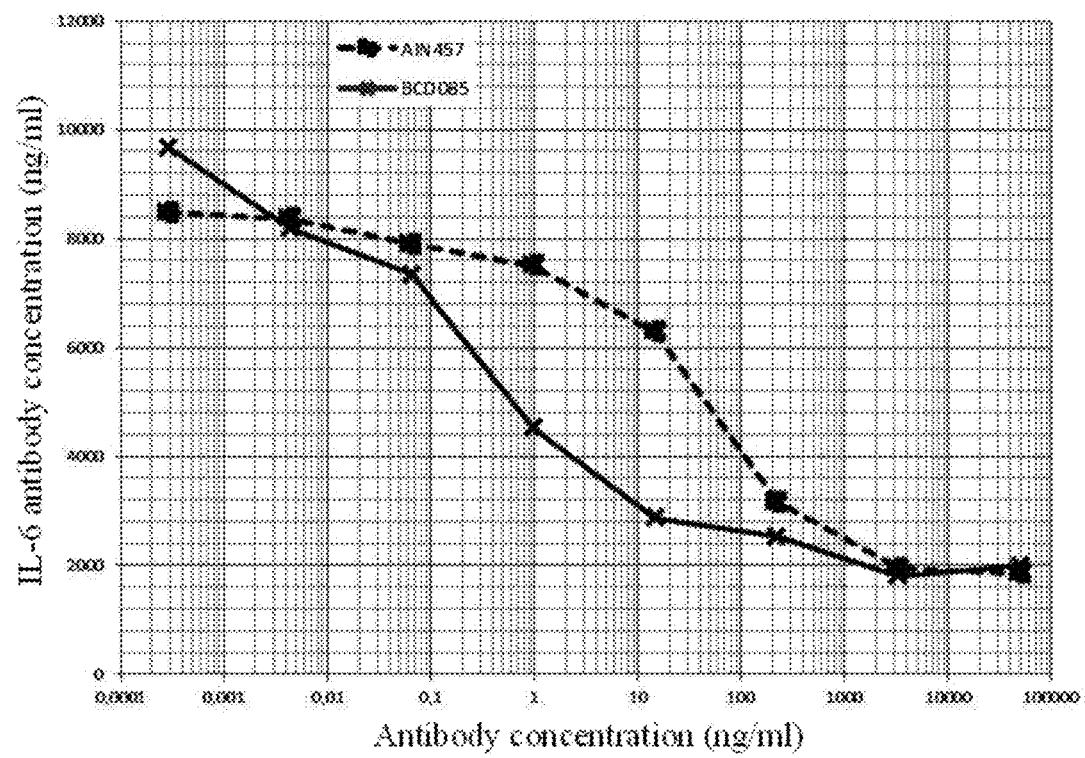
FIG. 14 shows a IL-6-inhibiting activity of BCD085 compared to AIN 457.
Figure 15A:
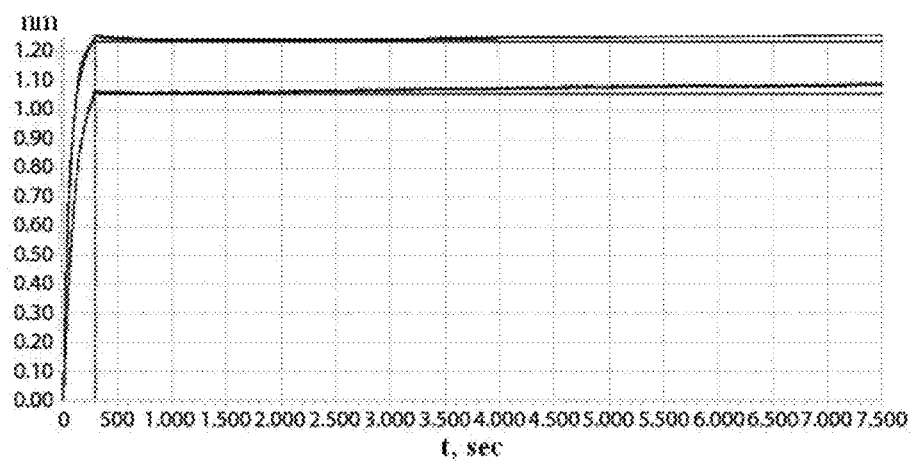
FIGS. 15A and 15B.
Figures 15B, 16A, 16B:
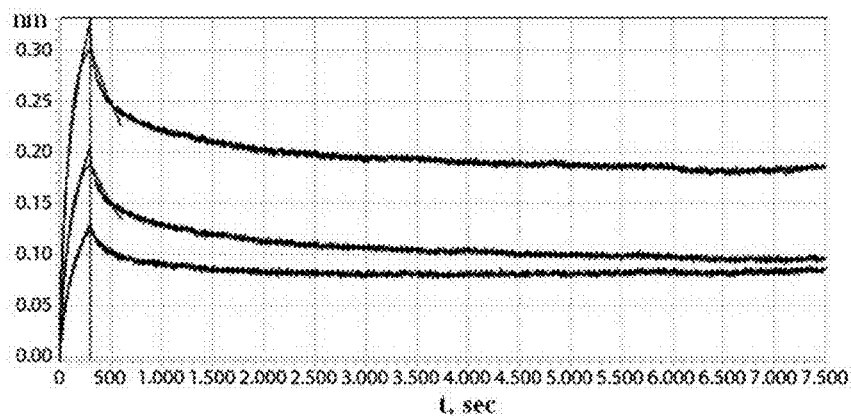
FIGS. 16A and 16B.

Results obtained by size-exclusion HPLC are presented in FIG. 14. The aggregate content in BCD085 substance was 0.312%.

Example 10

Cell Test of Blocking the Ability of IL-17A to Induce IL-6 Production

The ability of IL-17 to induce the production of IL-6 by human HT1080 cells (ATCC:CCL-121) was used to analyze the neutralizing capacity of BCD085 regarding human recombinant IL-17. Cells were grown on DMEM culture medium with added 10% inactivated fetal serum, gentamycin and glutamine. Aliquots of 5*10$^4$ cells/well were seeded in 96-well culture plates. Cells were allowed to adhere for 5 hours. The mixture of 40 ng/ml recombinant IL-17 and 20 ng/ml TNF-α was incubated with BCD085 dilutions for 1 hour at 37° C. Then cytokine/antibody mixture was added to the cells and left overnight. The production of IL-6 by HT1080 cell culture was proportional to the amount of IL-17 added. The amount of released IL-6 in cell supernatant samples was evaluated by ELISA technique using DuoSet ELISA Development System Human IL6 (RD System, Cat. No. DY206). Results obtained from evaluation of antagonistic properties of BCD085 candidate are shown in FIG. 14 in comparison with AIN457 (anti-IL-17A antibody by Novartis). The mean $IC_{50}$ for this candidate obtained from a series of experiments was 40±15 pM.

Example 11

Determination of BCD085 Affinity to IL-17A from Various Organisms

The affinity of BCD085 binding with human, monkey and rat IL-17A was analyzed on OctetRed 96 (ForteBio). BCD085 was non-specifically immobilized on the surface of amine reactive second-generation sensors (AR2G) according to the standard protocol described in the manufacturer's manual. The test was conducted at a temperature of 30° C. and using PBS with 0.1% Tween-20 and 0.1% BSA as a working buffer.

Human, monkey and rat IL-17A was titrated with the working buffer from a concentration of 126 nM to 2 nM with an increment of 2.

Binding curves (after subtracting a reference signal) were analyzed using Octet Data Analysis software (Version 7.0) in accordance with the standard procedure and using 1:1 interaction model. The results are presented in FIGS. 15A, 15B, 16A and 16B.

BCD085 binds to human IL-17A with picomolar affinity, which is 1000-fold stronger than nanomolar affinity to monkey IL-17A. In addition, the candidate does not interact with rat IL-17A (no curves are presented).

Example 12

Determination of the Aggregation Stability of BCD085 Under Thermal Stress

BCD085 preparation of 9 mg/ml in PBS was heated for 6 hours at a temperature of 50° C. Aggregation after the thermal stress was evaluated by size-exclusion HPLC. Chromatographic analysis was performed on Agilent 1100 system with Tosoh TSK-Gel G3000SWXL column (7.8 mm×30 cm, Cat. No. 08541) and Tosoh TSKgel Guard SWXL pre-column (6.0 mm×4.0 cm, 7 μm particles, Cat. No. 08543). Isocratic elution with mobile phase containing 50 mM sodium phosphate buffer and 0.3 M NaCl (pH 7.0) was performed under 0.5 ml/min flow rate with the detection at 214 nm and 280 nm wave lengths. Antibody samples were diluted with PBS (pH 7.5) to a concentration of ~1 mg/ml. Injection volume was 10 μl. Gel filtration standard mixture (Bio-Rad, Cat. No. 151-1901) was used to calibrate the column prior to the test.

Figures 17A, 17B:
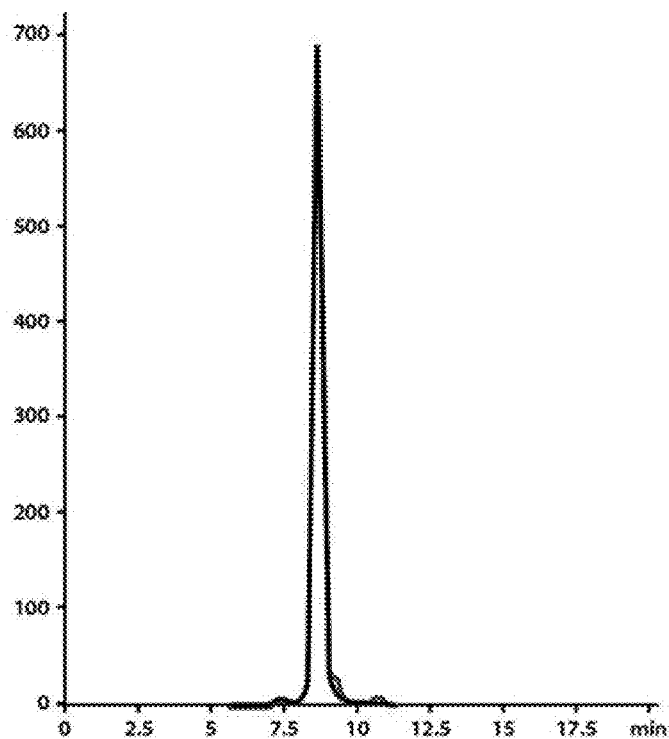
FIGS. 17A and 17B.

Results represented in FIGS. 17A and 17B show that BCD085 antibody is stable under thermal stress: aggregate content was less than 5%.

Example 13

Pharmacokinetic Study of BCD085 Monoclonal Anti-IL-17A Antibody After a Single-Dose Subcutaneous Administration to Monkeys A monoclonal anti-IL-17A antibody BCD085 was administered to rhesus monkeys (*Macaca mulatta*) as a single subcutaneous injection in a dose of 40 mg/kg. In specified time intervals (0.5, 1, 3, 6, 12, 24, 36, 48, 60, 72, 96, 120, 168, 264, 336, 432, 504, 672, 840 and 1008 hours after the administration) animal blood samples were selected and serum was obtained by the standard procedure. Serum levels of BCD085 antibody were evaluated by ELISA on immobilized human IL-17A (R&D Systems), where the bound antibody was detected using polyclonal goat antibodies against Fc-fragment of human IgG (Pierce-ThermoScientific).

Figure 18:
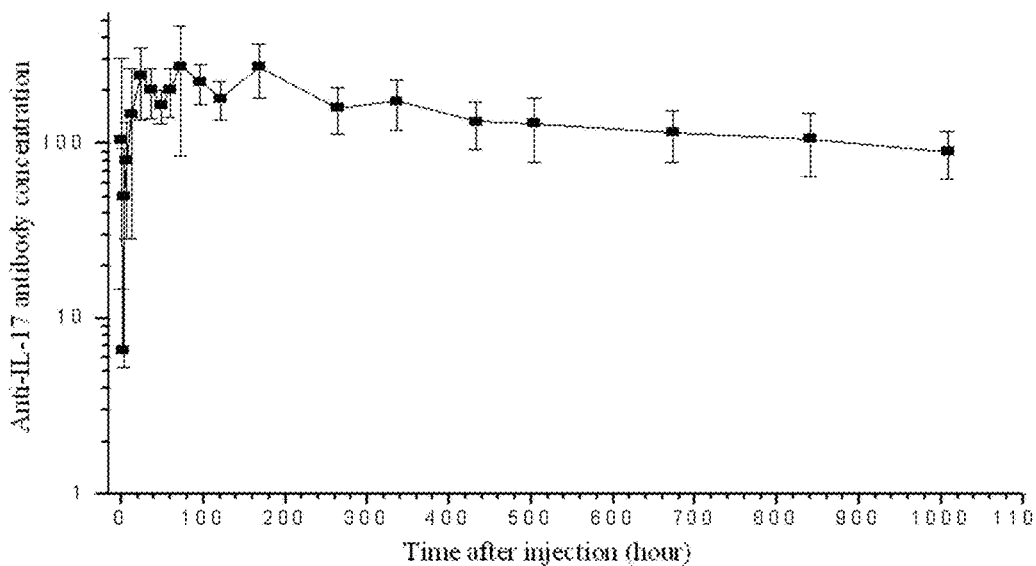
FIG. 18 shows a Pharmacokinetic profile of an anti-IL-17A antibody (BCD085) upon a single subcutaneous administration to rhesus monkeys (Macaca mulatta) in a dose of 40 mg/kg.

Results obtained from the assay of anti-IL-17A monoclonal antibody serum concentration after a single-dose subcutaneous administration to monkeys are shown in FIG. 18. It is shown that BCD085 exhibits significant long-term effect, i.e. circulates in blood for a long time. After a single-dose subcutaneous administration, maximum concentration of anti-Il-17A monoclonal antibody in animal serum was observed in 72-168 hours with this level remaining for 400 hours and only then reducing very slowly, so even after 1000 hours BCD085 concentration was significantly higher than the baseline. Estimated PK parameters of BCD085 after a single-dose subcutaneous administration to monkeys are listed in Table 2. It can be seen that the clearance (Cl) of the monoclonal anti-IL-17A antibody of the invention is 0.25±0.08 ml/h/kg, which assures its long-term blood circulation (over 42 days). Mean residence time and elimination half-life of anti-IL-17A monoclonal antibody were 946±374 h and 632±253 h, respectively.

TABLE 2

Principal pharmacokinetic parameters for the claimed monoclonal anti-IL17 antibody after a single-dose subcutaneous administration of 40 mg/kg to monkeys.

| Cmax (µg/ml) | Tmax (h) | AUC$_{(0\text{-}1008)}$ (h * µg)/ml | Cl (ml/h/kg) | MRT (h) | T½ (h) | Kel (h$^{-1}$) |
|---|---|---|---|---|---|---|
| 353 ± 164 (344-840) | 144 ± 48 (72-168) | 146 221 ± 19 439 (117 938-162 285) | 0.25 ± 0.08 (0.14-0.34) | 946 ± 374 (528-1274) | 632 ± 253 (344-840) | 0.00126 ± 0.00056 (0.0008-0.002) |

Example 14

Pharmaceutical Composition Comprising Antibodies of the Invention

| | |
|---|---|
| Concentration of anti-IL-17 (BCD085) | 10-50 mg/ml |
| Citrate buffer 10 mM | q.s. pH 6.0-7.0 |
| Sodium chloride | 50-150 MM |
| Sucrose, trehalose | 0.3-0.5% |
| Water for injection | q.s. 1 ml. |

Example 15

Kits Containing an Antibody Pharmaceutical Composition

Kits comprising anti-IL-17 antibody-containing pharmaceutical composition are produced by sterile sealing of the pharmaceutical composition obtained according to Example 14 into 1 ml ampoules or syringes which are then labeled and packed into plastic or carton containers.

A container with ampoule also comprises a package insert.

The invention claimed is:

1. An isolated monoclonal antibody or fragment thereof that specifically binds to human IL-17A, and comprises a heavy chain variable region (VH) and a light chain variable region (VL), wherein the antibody or fragment thereof comprises:
   a) HCDR1, HCDR2 and HCDR3 of the VH comprising the amino acid sequences of SEQ ID NO: 7, SEQ ID NO: 8 and SEQ ID NO: 9, respectively; and LCDR1, LCDR2 and LCDR3 of the VL comprising the amino acid sequences of SEQ ID NO: 10, SEQ ID NO: 11 and SEQ ID NO: 12, respectively; or
   b) a variant of a), comprising one amino acid substitution selected from the group consisting of:
   the fifth amino acid of SEQ ID NO: 7 is D, K, L, P, T or M;
   the sixth amino acid of SEQ ID NO: 7 is F;
   the seventh amino acid of SEQ ID NO: 7 is G, N, S, T, V or M;
   the eighth amino acid of SEQ ID NO: 7 is I;
   the ninth amino acid of SEQ ID NO: 7 is G, N or T;
   the first amino acid of SEQ ID NO: 8 is G, I, L, M or S;
   the third amino acid of SEQ ID NO: 8 is D;
   the fourth amino acid of SEQ ID NO: 8 is M;
   the fifth amino acid of SEQ ID NO: 8 is L, R or V;
   the sixth amino acid of SEQ ID NO: 8 is L;
   the eighth amino acid of SEQ ID NO: 8 is T, L, R or W;
   the ninth amino acid of SEQ ID NO: 8 is T or Y;
   the tenth amino acid of SEQ ID NO: 8 is S, L, R or W;
   the eleventh amino acid of SEQ ID NO: 8 is T, L or K;
   the third amino acid of SEQ ID NO: 9 is R, A, I or N;
   the fourth amino acid of SEQ ID NO: 9 is E, L, S, T, V or M;
   the sixth amino acid of SEQ ID NO: 9 is F or V;
   the seventh amino acid of SEQ ID NO: 9 is S;
   the eighth amino acid of SEQ ID NO: 9 is A, F, L, P or Y;
   the ninth amino acid of SEQ ID NO: 9 is F, H, I, S, W or M;
   the tenth amino acid of SEQ ID NO: 9 is A, I, N, R, S or V;
   the fifth amino acid of SEQ ID NO: 10 is N or R;
   the sixth amino acid of SEQ ID NO: 10 is S or T;
   the seventh amino acid of SEQ ID NO: 10 is L or R;
   the eighth amino acid of SEQ ID NO: 10 is V;
   the ninth amino acid of SEQ ID NO: 10 is Y, L, S, T or V;
   the tenth amino acid of SEQ ID NO: 10 is L or V;
   the eleventh amino acid of SEQ ID NO: 10 is S, P or R;
   the twelfth amino acid of SEQ ID NO: 10 is W, A or L;
   the first amino acid of SEQ ID NO: 11 is E, L or M;
   the second amino acid of SEQ ID NO: 11 is S or L;
   the third amino acid of SEQ ID NO: 11 is G;
   the fourth amino acid of SEQ ID NO: 11 is I, K, L, M, R or W;
   the second amino acid of SEQ ID NO: 12 is A;
   the third amino acid of SEQ ID NO: 12 is G or T;
   the fourth amino acid of SEQ ID NO: 12 is F, A or I;
   the fifth amino acid of SEQ ID NO: 12 is R;
   the sixth amino acid of SEQ ID NO: 12 is S;
   the seventh amino acid of SEQ ID NO: 12 is F;
   the eighth amino acid of SEQ ID NO: 12 is H; and
   the tenth amino acid of SEQ ID NO: 12 is I, L or W.

2. The isolated monoclonal antibody or fragment thereof according to claim 1, wherein:
   LCDR1 comprises the amino acid sequence of SEQ ID NO: 10;
   LCDR2 comprises the amino acid sequence of SEQ ID NO: 11; and
   LCDR3 comprises the amino acid sequence of SEQ ID NO: 12.

3. The isolated monoclonal antibody or fragment thereof according to claim 1, wherein:
   a) the VH comprises an amino acid sequence that is at least 90% identical to SEQ ID NO: 13; and
   b) the VL comprises an amino acid sequence that is at least 90% identical to SEQ ID NO: 14.

4. The isolated monoclonal antibody or fragment thereof according to claim 1, wherein the heavy chain of the isolated monoclonal antibody comprises the amino acid sequence of SEQ ID NO: 15.

5. The isolated monoclonal antibody or fragment thereof according to claim 1, wherein the light chain of the isolated monoclonal antibody comprises the amino acid sequence of SEQ ID NO: 16.

6. The isolated monoclonal antibody or fragment thereof according to claim 1, wherein said fragment is selected from F(ab')2, F(ab)2, Fab', Fab, Fv and scFv.

7. The isolated monoclonal antibody or fragment thereof according to claim 6, wherein said fragment is produced by mammalian, yeast or bacterial cells.

8. The isolated monoclonal antibody or fragment thereof according to claim 1, wherein the CDRs of the light chain variable region and of the heavy chain variable region are from a non-human source.

9. The isolated monoclonal antibody or fragment thereof according to claim 1, wherein said isolated monoclonal antibody is an IgG1, IgG2, IgG3, IgG4, IgA or IgD.

10. The isolated monoclonal antibody or fragment thereof according to claim 9, wherein said isolated monoclonal antibody is a human IgG1 further comprising amino acid modifications in Fc-region selected from: M252Y/S254T/T256E, N434W, N434A, N434F, H433K/N434F/Y436H, H433K/N434F/Y436H+M252Y/S254T/T256E, T307A/E380A/N434A, and T250Q/M428L.

11. A pharmaceutical composition comprising the isolated monoclonal antibody or fragment thereof according to claim 1, in combination with one or several pharmaceutically suitable carriers, vehicles or diluents.

12. The pharmaceutical composition according to claim 11, further comprising active pharmaceutical ingredients selected from TNF-α inhibitors or any other anti-IL-17A antibodies.

13. An isolated monoclonal antibody or fragment thereof that specifically binds to human IL-17A, and comprises a heavy chain variable region (VH) and a light chain variable region (VL), wherein the antibody or fragment thereof comprises HCDR1, HCDR2 and HCDR3 of the VH comprising the amino acid sequences of SEQ ID NO: 7, SEQ ID NO: 8 and SEQ ID NO: 9, respectively; and, wherein LCDR1, LCDR2 and LCDR3 of the VL comprising the amino acid sequences of SEQ ID NO: 10, SEQ ID NO: 11 and SEQ ID NO: 12, respectively.

14. The isolated monoclonal antibody or fragment thereof according to claim 13, wherein:
   a) the VH comprises an amino acid sequence that is at least 90% identical to SEQ ID NO: 13; and
   b) the VL comprises an amino acid sequence that is at least 90% identical to SEQ ID NO: 14.

15. The isolated monoclonal antibody or fragment thereof according to claim 14, wherein the VH comprises the amino acid sequence of SEQ ID NO: 13, and the VL comprises the amino acid sequence of SEQ ID NO: 14.

16. An isolated binding protein containing an antibody that specifically binds to human IL-17A, the antibody comprising a heavy chain variable region (VH) and a light chain variable region (VL), wherein the antibody comprises:
   a) HCDR1, HCDR2 and HCDR3 of the VH comprising the amino acid sequences of SEQ ID NO: 7, SEQ ID NO: 8 and SEQ ID NO: 9, respectively; and LCDR1, LCDR2 and LCDR3 of the VL comprising the amino acid sequences of SEQ ID NO: 10, SEQ ID NO: 11 and SEQ ID NO: 12, respectively; or
   b) a variant of a), comprising one amino acid substitution selected from the group consisting of:
      the fifth amino acid of SEQ ID NO: 7 is D, K, L, P, T or M;
      the sixth amino acid of SEQ ID NO: 7 is F;
      the seventh amino acid of SEQ ID NO: 7 is G, N, S, T, V or M;
      the eighth amino acid of SEQ ID NO: 7 is I;
      the ninth amino acid of SEQ ID NO: 7 is G, N or T;
      the first amino acid of SEQ ID NO: 8 is G, I, L, M or S;
      the third amino acid of SEQ ID NO: 8 is D;
      the fourth amino acid of SEQ ID NO: 8 is M;
      the fifth amino acid of SEQ ID NO: 8 is L, R or V;
      the sixth amino acid of SEQ ID NO: 8 is L;
      the eighth amino acid of SEQ ID NO: 8 is T, L, R or W;
      the ninth amino acid of SEQ ID NO: 8 is T or Y;
      the tenth amino acid of SEQ ID NO: 8 is S, L, R or W;
      the eleventh amino acid of SEQ ID NO: 8 is T, L or K;
      the third amino acid of SEQ ID NO: 9 is R, A, I or N;
      the fourth amino acid of SEQ ID NO: 9 is E, L, S, T, V or M;
      the sixth amino acid of SEQ ID NO: 9 is F or V;
      the seventh amino acid of SEQ ID NO: 9 is S;
      the eighth amino acid of SEQ ID NO: 9 is A, F, L, P or Y;
      the ninth amino acid of SEQ ID NO: 9 is F, H, I, S, W or M;
      the tenth amino acid of SEQ ID NO: 9 is A, I, N, R, S or V;
      the fifth amino acid of SEQ ID NO: 10 is N or R;
      the sixth amino acid of SEQ ID NO: 10 is S or T;
      the seventh amino acid of SEQ ID NO: 10 is L or R;
      the eighth amino acid of SEQ ID NO: 10 is V;
      the ninth amino acid of SEQ ID NO: 10 is Y, L, S, T or V;
      the tenth amino acid of SEQ ID NO: 10 is L or V;
      the eleventh amino acid of SEQ ID NO: 10 is S, P or R;
      the twelfth amino acid of SEQ ID NO: 10 is W, A or L;
      the first amino acid of SEQ ID NO: 11 is E, L or M;
      the second amino acid of SEQ ID NO: 11 is S or L;
      the third amino acid of SEQ ID NO: 11 is G;
      the fourth amino acid of SEQ ID NO: 11 is I, K, L, M, R or W;
      the second amino acid of SEQ ID NO: 12 is A;
      the third amino acid of SEQ ID NO: 12 is G or T;
      the fourth amino acid of SEQ ID NO: 12 is F, A or I;
      the fifth amino acid of SEQ ID NO: 12 is R;
      the sixth amino acid of SEQ ID NO: 12 is S;
      the seventh amino acid of SEQ ID NO: 12 is F;
      the eighth amino acid of SEQ ID NO: 12 is H; and
      the tenth amino acid of SEQ ID NO: 12 is I, L or W.

* * * * *

SEQUENCE LISTING

<160> NUMBER OF SEQ ID NOS: 16

<210> SEQ ID NO 1
<211> LENGTH: 9
<212> TYPE: PRT
<213> ORGANISM: Homo sapiens
<220> FEATURE:
<221> NAME/KEY: VARIANT
<222> LOCATION: (5)..(5)
<223> OTHER INFORMATION: Xaa may be Asn, Asp, Lys, Leu, Met, Pro or Thr
<220> FEATURE:
<221> NAME/KEY: VARIANT
<222> LOCATION: (6)..(6)
<223> OTHER INFORMATION: Xaa may be Tyr or Phe
<220> FEATURE:
<221> NAME/KEY: VARIANT
<222> LOCATION: (7)..(7)
<223> OTHER INFORMATION: Xaa may be Ala, Gly, Met, Asn, Ser, Thr or Val -continued

```
<220> FEATURE:
<221> NAME/KEY: VARIANT
<222> LOCATION: (8)..(8)
<223> OTHER INFORMATION: Xaa may be Met or Ile
<220> FEATURE:
<221> NAME/KEY: VARIANT
<222> LOCATION: (9)..(9)
<223> OTHER INFORMATION: Xaa may be Ser, Gly, Asn or Thr

<400> SEQUENCE: 1

Phe Thr Phe Ser Xaa Xaa Xaa Xaa Xaa
1               5

<210> SEQ ID NO 2
<211> LENGTH: 11
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa may be Arg, Gly, Ile, Leu, Met or Ser
<220> FEATURE:
<221> NAME/KEY: VARIANT
<222> LOCATION: (3)..(3)
<223> OTHER INFORMATION: Xaa may be Asp or Glu
<220> FEATURE:
<221> NAME/KEY: VARIANT
<222> LOCATION: (4)..(4)
<223> OTHER INFORMATION: Xaa may be Gly or Met
<220> FEATURE:
<221> NAME/KEY: VARIANT
<222> LOCATION: (5)..(5)
<223> OTHER INFORMATION: Xaa may be Gly, Leu, Arg or Val
<220> FEATURE:
<221> NAME/KEY: VARIANT
<222> LOCATION: (6)..(6)
<223> OTHER INFORMATION: Xaa may be Ile or Leu
<220> FEATURE:
<221> NAME/KEY: VARIANT
<222> LOCATION: (8)..(8)
<223> OTHER INFORMATION: Xaa may be Ser, Thr, Leu, Arg or Trp
<220> FEATURE:
<221> NAME/KEY: VARIANT
<222> LOCATION: (9)..(9)
<223> OTHER INFORMATION: Xaa can be Ser, Thr or Tyr
<220> FEATURE:
<221> NAME/KEY: VARIANT
<222> LOCATION: (10)..(10)
<223> OTHER INFORMATION: Xaa may be Ser, Thr, Leu, Arg or Trp
<220> FEATURE:
<221> NAME/KEY: VARIANT
<222> LOCATION: (11)..(11)
<223> OTHER INFORMATION: Xaa may be Tyr, Thr, Leu or Lys

<400> SEQUENCE: 2

Xaa Ile Xaa Xaa Xaa Xaa Gly Xaa Xaa Xaa Xaa
1               5                   10

<210> SEQ ID NO 3
<211> LENGTH: 10
<212> TYPE: PRT
<213> ORGANISM: Homo sapiens
<220> FEATURE:
<221> NAME/KEY: VARIANT
<222> LOCATION: (3)..(3)
<223> OTHER INFORMATION: Xaa may be Arg, Val, Ala, Asn or Ile
<220> FEATURE:
<221> NAME/KEY: VARIANT
<222> LOCATION: (4)..(4)
<223> OTHER INFORMATION: Xaa may be Asn, Glu, Leu, Met, Ser, Thr or Val
<220> FEATURE:
<221> NAME/KEY: VARIANT
<222> LOCATION: (6)..(6)
<223> OTHER INFORMATION: Xaa may be Tyr, Phe or Val
```

```
<220> FEATURE:
<221> NAME/KEY: VARIANT
<222> LOCATION: (7)..(7)
<223> OTHER INFORMATION: Xaa may be Gly or Ser
<220> FEATURE:
<221> NAME/KEY: VARIANT
<222> LOCATION: (8)..(8)
<223> OTHER INFORMATION: Xaa may be Met, Ala, Phe, Leu, Pro or Tyr
<220> FEATURE:
<221> NAME/KEY: VARIANT
<222> LOCATION: (9)..(9)
<223> OTHER INFORMATION: Xaa may be Tyr, Phe, His, Ile, Met, Ser or Trp
<220> FEATURE:
<221> NAME/KEY: VARIANT
<222> LOCATION: (10)..(10)
<223> OTHER INFORMATION: Xaa may be Tyr, Ala, Ile, Asn, Arg, Ser or Val

<400> SEQUENCE: 3

Cys Ala Xaa Xaa Tyr Xaa Xaa Xaa Xaa Xaa
1               5                   10

<210> SEQ ID NO 4
<211> LENGTH: 12
<212> TYPE: PRT
<213> ORGANISM: Homo sapiens
<220> FEATURE:
<221> NAME/KEY: VARIANT
<222> LOCATION: (5)..(5)
<223> OTHER INFORMATION: Xaa may be Glu, Asn or Arg
<220> FEATURE:
<221> NAME/KEY: VARIANT
<222> LOCATION: (6)..(6)
<223> OTHER INFORMATION: Xaa may be Asp, Ser or Thr
<220> FEATURE:
<221> NAME/KEY: VARIANT
<222> LOCATION: (7)..(7)
<223> OTHER INFORMATION: Xaa may be Val, Leu or Arg
<220> FEATURE:
<221> NAME/KEY: VARIANT
<222> LOCATION: (8)..(8)
<223> OTHER INFORMATION: Xaa may be Gly or Val
<220> FEATURE:
<221> NAME/KEY: VARIANT
<222> LOCATION: (9)..(9)
<223> OTHER INFORMATION: Xaa may be Phe, Tyr, Leu, Ser, Thr or Val
<220> FEATURE:
<221> NAME/KEY: VARIANT
<222> LOCATION: (10)..(10)
<223> OTHER INFORMATION: Xaa may be Gly, Leu or Val
<220> FEATURE:
<221> NAME/KEY: VARIANT
<222> LOCATION: (11)..(11)
<223> OTHER INFORMATION: Xaa may be Asn, Ser, Pro or Arg
<220> FEATURE:
<221> NAME/KEY: VARIANT
<222> LOCATION: (12)..(12)
<223> OTHER INFORMATION: Xaa may be Tyr, Trp, Ala or Leu

<400> SEQUENCE: 4

Thr Gly Thr Ser Xaa Xaa Xaa Xaa Xaa Xaa Xaa Xaa
1               5                   10

<210> SEQ ID NO 5
<211> LENGTH: 7
<212> TYPE: PRT
<213> ORGANISM: Homo Sapiens
<220> FEATURE:
<221> NAME/KEY: VARIANT
<222> LOCATION: (1)..(1)
<223> OTHER INFORMATION: Xaa may be Arg, Glu, Leu or Met
<220> FEATURE:
<221> NAME/KEY: VARIANT
<222> LOCATION: (2)..(2)
<223> OTHER INFORMATION: Xaa may be Val, Ser or Leu
```

```
<220> FEATURE:
<221> NAME/KEY: VARIANT
<222> LOCATION: (3)..(3)
<223> OTHER INFORMATION: Xaa may be Asn or Gly
<220> FEATURE:
<221> NAME/KEY: VARIANT
<222> LOCATION: (4)..(4)
<223> OTHER INFORMATION: Xaa may be Thr, Ile, Lys, Leu, Met, Arg or Trp

<400> SEQUENCE: 5

Xaa Xaa Xaa Xaa Arg Pro Ser
1               5

<210> SEQ ID NO 6
<211> LENGTH: 10
<212> TYPE: PRT
<213> ORGANISM: Homo sapiens
<220> FEATURE:
<221> NAME/KEY: VARIANT
<222> LOCATION: (2)..(2)
<223> OTHER INFORMATION: Xaa may be Ser or Ala
<220> FEATURE:
<221> NAME/KEY: VARIANT
<222> LOCATION: (3)..(3)
<223> OTHER INFORMATION: Xaa may be Ser, Gly or Thr
<220> FEATURE:
<221> NAME/KEY: VARIANT
<222> LOCATION: (4)..(4)
<223> OTHER INFORMATION: Xaa may be Try, Phe, Ala or Ile
<220> FEATURE:
<221> NAME/KEY: VARIANT
<222> LOCATION: (5)..(5)
<223> OTHER INFORMATION: Xaa may be Lys or Arg
<220> FEATURE:
<221> NAME/KEY: VARIANT
<222> LOCATION: (6)..(6)
<223> OTHER INFORMATION: Xaa may be Ala or Ser
<220> FEATURE:
<221> NAME/KEY: VARIANT
<222> LOCATION: (7)..(7)
<223> OTHER INFORMATION: Xaa may be Gly or Phe
<220> FEATURE:
<221> NAME/KEY: VARIANT
<222> LOCATION: (8)..(8)
<223> OTHER INFORMATION: Xaa may be Gly or His
<220> FEATURE:
<221> NAME/KEY: VARIANT
<222> LOCATION: (10)..(10)
<223> OTHER INFORMATION: Xaa may be Tyr, Ile, Leu or Trp

<400> SEQUENCE: 6

Cys Xaa Xaa Xaa Xaa Xaa Xaa Xaa Thr Xaa
1               5                   10

<210> SEQ ID NO 7
<211> LENGTH: 9
<212> TYPE: PRT
<213> ORGANISM: Homo sapiens

<400> SEQUENCE: 7

Phe Thr Phe Ser Asn Tyr Ala Met Ser
1               5

<210> SEQ ID NO 8
<211> LENGTH: 11
<212> TYPE: PRT
<213> ORGANISM: Homo sapiens

<400> SEQUENCE: 8

Arg Ile Glu Gly Gly Ile Gly Ser Ser Thr Tyr
1               5                   10
```

<210> SEQ ID NO 9
<211> LENGTH: 10
<212> TYPE: PRT
<213> ORGANISM: Homo sapiens

<400> SEQUENCE: 9

Cys Ala Val Asn Tyr Tyr Gly Met Tyr Tyr
1               5                   10

<210> SEQ ID NO 10
<211> LENGTH: 12
<212> TYPE: PRT
<213> ORGANISM: Homo sapiens

<400> SEQUENCE: 10

Thr Gly Thr Ser Glu Asp Val Gly Phe Gly Asn Tyr
1               5                   10

<210> SEQ ID NO 11
<211> LENGTH: 7
<212> TYPE: PRT
<213> ORGANISM: Homo sapiens

<400> SEQUENCE: 11

Arg Val Asn Thr Arg Pro Ser
1               5

<210> SEQ ID NO 12
<211> LENGTH: 10
<212> TYPE: PRT
<213> ORGANISM: Homo sapiens

<400> SEQUENCE: 12

Cys Ser Ser Tyr Lys Ala Gly Gly Thr Tyr
1               5                   10

<210> SEQ ID NO 13
<211> LENGTH: 117
<212> TYPE: PRT
<213> ORGANISM: Homo sapiens

<400> SEQUENCE: 13

Gln Val Gln Leu Val Gln Ser Gly Gly Gly Leu Val Gln Pro Gly Gly
1               5                   10                  15

Ser Leu Arg Leu Ser Cys Ala Ala Asp Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Arg Ile Glu Gly Gly Ile Gly Ser Ser Thr Tyr Ala Val Asp Ser
    50                  55                  60

Val Lys Asp Arg Phe Thr Ile Ser Arg Asp Asp Ala Lys Asn Thr Leu
65                  70                  75                  80

Tyr Leu Gln Met Ser Ser Leu Lys Thr Glu Asp Thr Ala Val Tyr Tyr
                85                  90                  95

Cys Ala Val Asn Tyr Tyr Gly Met Tyr Tyr Trp Gly Gln Gly Thr Leu
            100                 105                 110

Val Thr Val Ser Ser
            115

```
<210> SEQ ID NO 14
<211> LENGTH: 112
<212> TYPE: PRT
<213> ORGANISM: Homo sapiens

<400> SEQUENCE: 14

Gln Ser Val Leu Thr Gln Pro Pro Ser Val Ser Val Ala Pro Gly Lys
1               5                   10                  15

Thr Val Thr Ile Ser Cys Thr Gly Thr Ser Glu Asp Val Gly Phe Gly
            20                  25                  30

Asn Tyr Val Ser Trp Tyr Gln His Leu Pro Gly Thr Ala Pro Lys Leu
        35                  40                  45

Leu Ile Tyr Arg Val Asn Thr Arg Pro Ser Gly Val Pro Asp Arg Phe
    50                  55                  60

Ser Gly Ser Gln Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Lys Ala Gly
                85                  90                  95

Gly Thr Tyr Val Phe Gly Gly Gly Thr Lys Leu Thr Val Leu Gly Gln
            100                 105                 110

<210> SEQ ID NO 15
<211> LENGTH: 447
<212> TYPE: PRT
<213> ORGANISM: Homo sapiens

<400> SEQUENCE: 15

Gln Val Gln Leu Val Gln Ser Gly Gly Gly Leu Val Gln Pro Gly Gly
1               5                   10                  15

Ser Leu Arg Leu Ser Cys Ala Ala Asp Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Arg Ile Glu Gly Gly Ile Gly Ser Ser Thr Tyr Ala Val Asp Ser
    50                  55                  60

Val Lys Asp Arg Phe Thr Ile Ser Arg Asp Asp Ala Lys Asn Thr Leu
65                  70                  75                  80

Tyr Leu Gln Met Ser Ser Leu Lys Thr Glu Asp Thr Ala Val Tyr Tyr
                85                  90                  95

Cys Ala Val Asn Tyr Tyr Gly Met Tyr Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220
```

```
Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Tyr Ile Thr Arg Glu
            245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 16
<211> LENGTH: 216
<212> TYPE: PRT
<213> ORGANISM: Homo sapiens

<400> SEQUENCE: 16

Gln Ser Val Leu Thr Gln Pro Pro Ser Val Ser Val Ala Pro Gly Lys
1               5                   10                  15

Thr Val Thr Ile Ser Cys Thr Gly Thr Ser Glu Asp Val Gly Phe Gly
                20                  25                  30

Asn Tyr Val Ser Trp Tyr Gln His Leu Pro Gly Thr Ala Pro Lys Leu
            35                  40                  45

Leu Ile Tyr Arg Val Asn Thr Arg Pro Ser Gly Val Pro Asp Arg Phe
50                  55                  60

Ser Gly Ser Gln Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Lys Ala Gly
                85                  90                  95

Gly Thr Tyr Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160
```

```
Ala Gly Val Glu Thr Thr Thr Pro Ser Lys Gln Ser Asn Asn Lys Tyr
                165             170                 175

Ala Ala Ser Ser Tyr Leu Ser Leu Thr Pro Glu Gln Trp Lys Ser His
            180             185                 190

Arg Ser Tyr Ser Cys Gln Val Thr His Glu Gly Ser Thr Val Glu Lys
        195             200             205

Thr Val Ala Pro Thr Glu Cys Ser
210                 215
```